(12) United States Patent
Hermann et al.

(10) Patent No.: US 6,706,048 B2
(45) Date of Patent: Mar. 16, 2004

(54) METHOD AND DEVICE FOR USE IN MINIMALLY INVASIVE APPROXIMATION OF MUSCLE AND OTHER TISSUE

(75) Inventors: George D. Hermann, Portola Valley, CA (US); Jose de la Pena, Lomas Virreyes (MX); Roger de la Torre, Wentzville, MO (US); Thomas Howell, Palo Alto, CA (US); Roger Khouri, Key Biscayne, FL (US); David Willis, Palo Alto, CA (US); Michael Drews, Sacramento, CA (US)

(73) Assignee: Thomas J. Fogarty, Portola Valley, CA (US)

( * ) Notice: Subject to any disclaimer, the term of this patent is extended or adjusted under 35 U.S.C. 154(b) by 120 days.

(21) Appl. No.: 09/969,989

(22) Filed: Oct. 2, 2001

(65) Prior Publication Data

US 2002/0065534 A1 May 30, 2002

Related U.S. Application Data

(63) Continuation of application No. 09/738,818, filed on Dec. 15, 2000, now abandoned.
(60) Provisional application No. 60/172,426, filed on Dec. 17, 1999.

(51) Int. Cl.$^7$ ................................................ A61B 17/10
(52) U.S. Cl. ........................................................ 606/139
(58) Field of Search ................................ 606/116, 117, 606/220; 24/337, 347, 922, 517

(56) References Cited

U.S. PATENT DOCUMENTS

| | | | | |
|---|---|---|---|---|
| 148,256 | A | * 3/1874 | Stevenson | ................... 227/144 |
| 982,896 | A | * 1/1911 | Stoll | ............................ 40/301 |
| 3,595,201 | A | * 7/1971 | Oudenhoven | ................. 40/301 |
| 4,127,227 | A | 11/1978 | Green | |
| 5,125,553 | A | 6/1992 | Oddsen et al. | |
| 5,329,943 | A | 7/1994 | Johnson | |
| 5,423,856 | A | 6/1995 | Green | |
| 5,423,858 | A | * 6/1995 | Bolanos et al. | ............. 606/220 |
| 5,591,206 | A | 1/1997 | Moufarrege | |
| 5,655,544 | A | 8/1997 | Johnson | |
| 5,925,064 | A | 7/1999 | Meyers et al. | |
| 5,964,772 | A | 10/1999 | Bolduc et al. | |
| 6,044,847 | A | 4/2000 | Carter et al. | |
| 6,048,351 | A | 4/2000 | Gordon et al. | |
| 6,145,225 | A | * 11/2000 | Ritchey | ....................... 40/301 |
| 6,179,844 | B1 | * 1/2001 | Underwood | ................. 606/117 |

FOREIGN PATENT DOCUMENTS

| EP | 0 169 044 | | 7/1985 | |
|---|---|---|---|---|
| EP | 0 315 344 | | 5/1989 | |
| GB | 2066164 | A * | 7/1981 | ........... B25B/27/02 |

OTHER PUBLICATIONS

J. Gradel, M. D., "Umbilical Technical Maneuvers to Facilitate Abdominoplasty with limited Incisions", Aesth. Plast. Surg., 15:251–256, (1991).

T. S. Wilkinson, M. D., "Limited Abdominoplasty Techniques Applied Complete Abdominal Repair", Aesth. Plast. Surg., 18: 49–55, (1994).

* cited by examiner

*Primary Examiner*—Gary Jackson
(74) *Attorney, Agent, or Firm*—Morrison & Foerster LLP

(57) ABSTRACT

Tissue approximation devices for the minimally invasive approximation of muscle or fascia, such as approximation of the rectus muscles in the abdomen (abdominoplasty), or hernia repair and other such applications using minimally invasive methods to access and perform the procedures thereby reducing or eliminating visible scars.

18 Claims, 24 Drawing Sheets

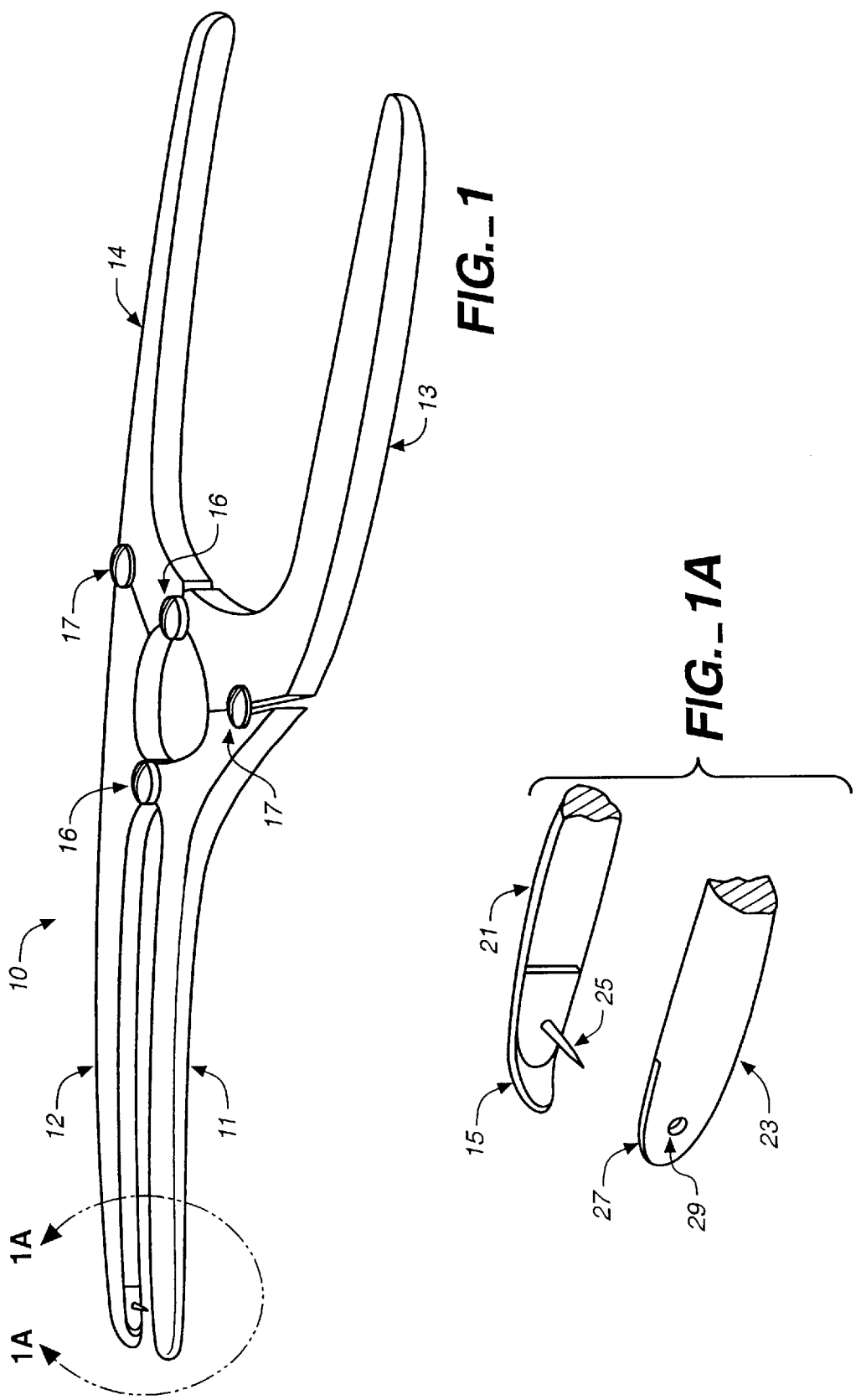

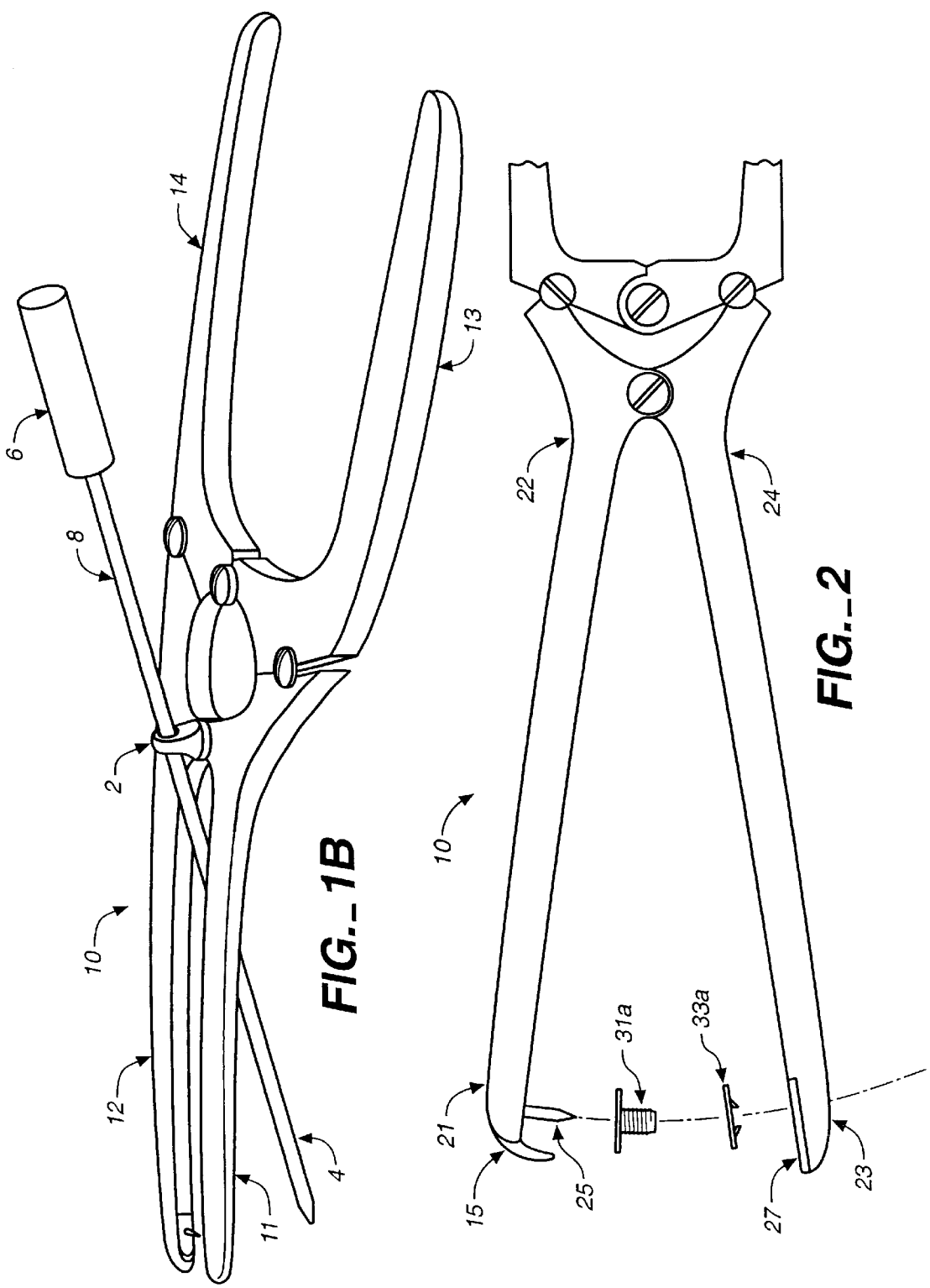

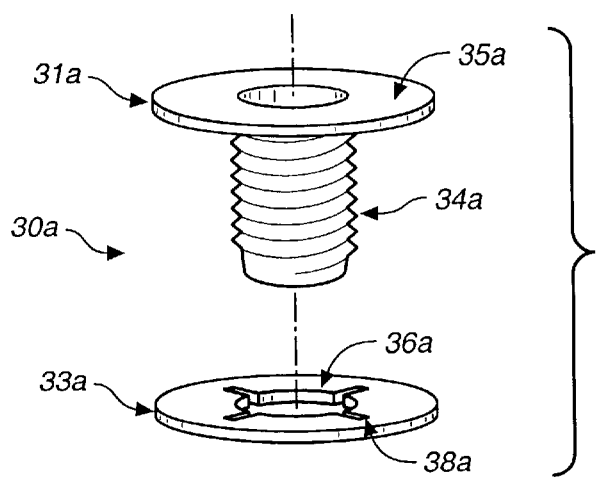
FIG._3A
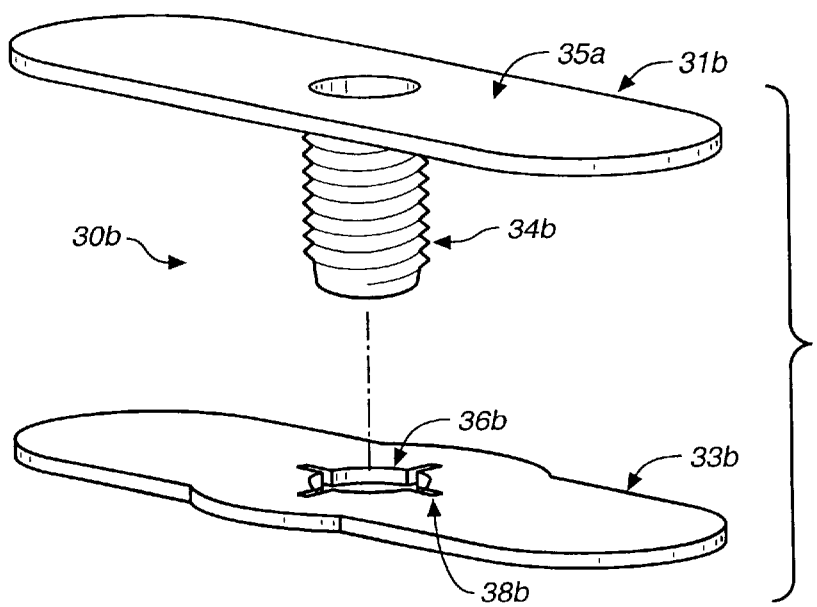
FIG._3B
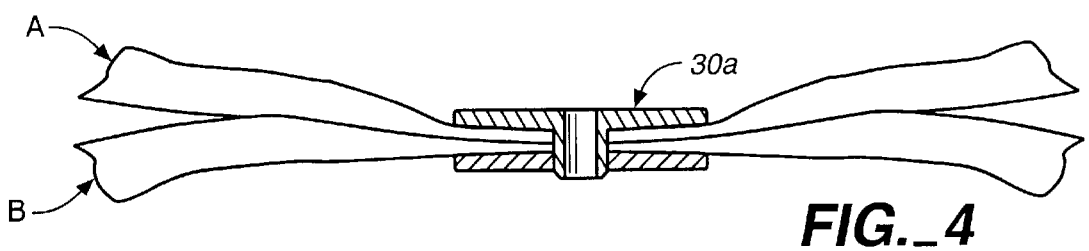
FIG._4

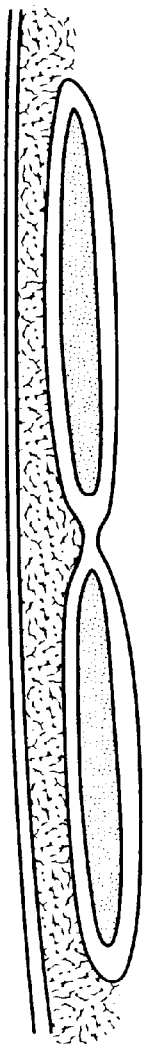
FIG._5A
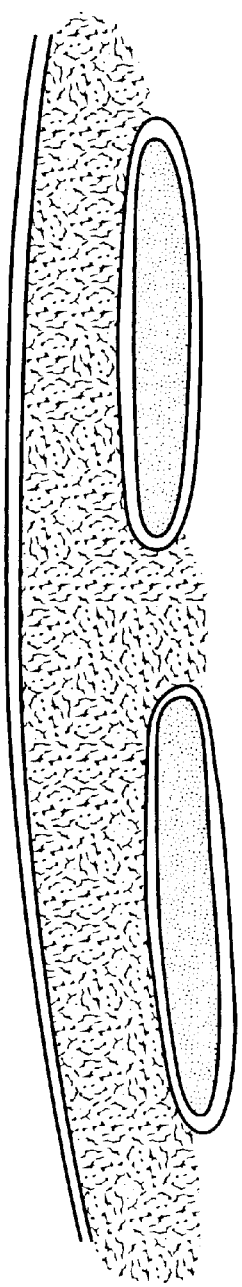
FIG._5B
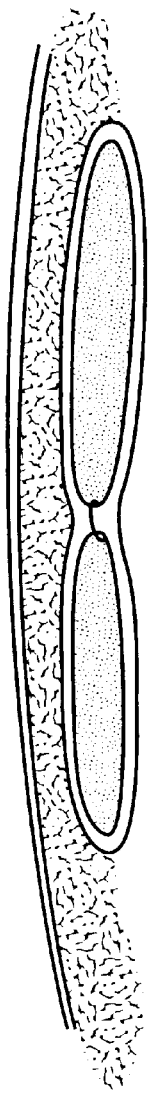
FIG._5C

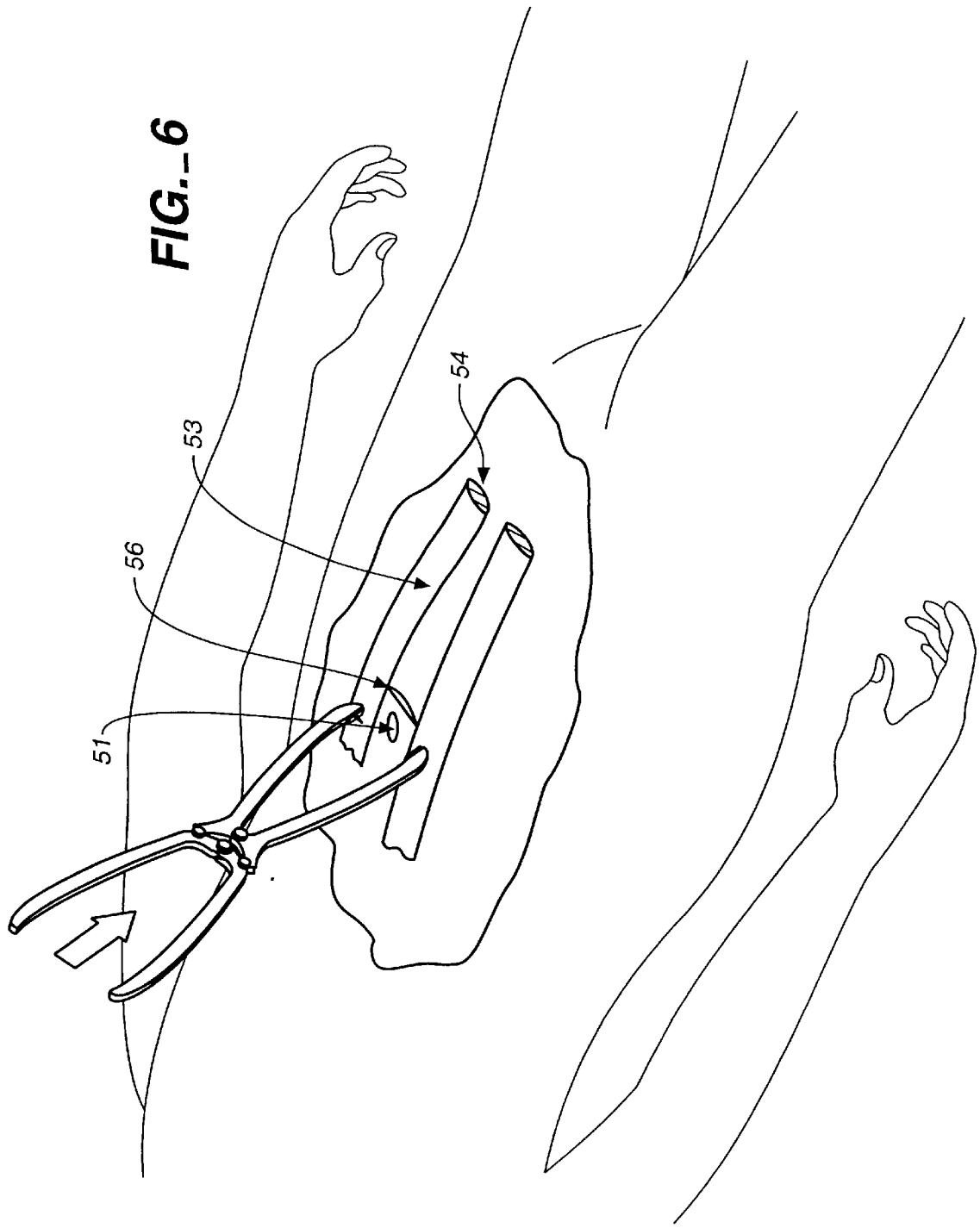
FIG._6

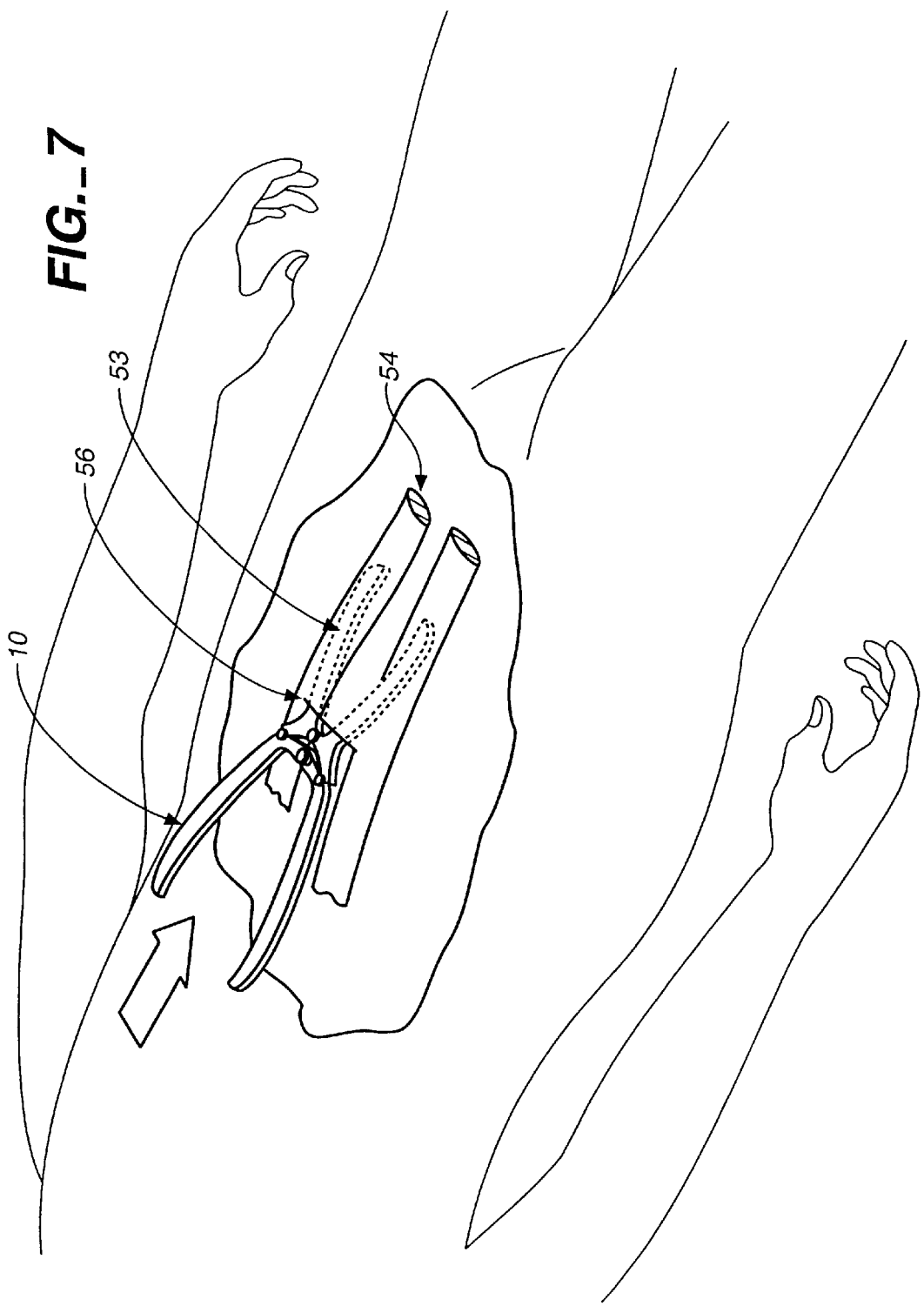

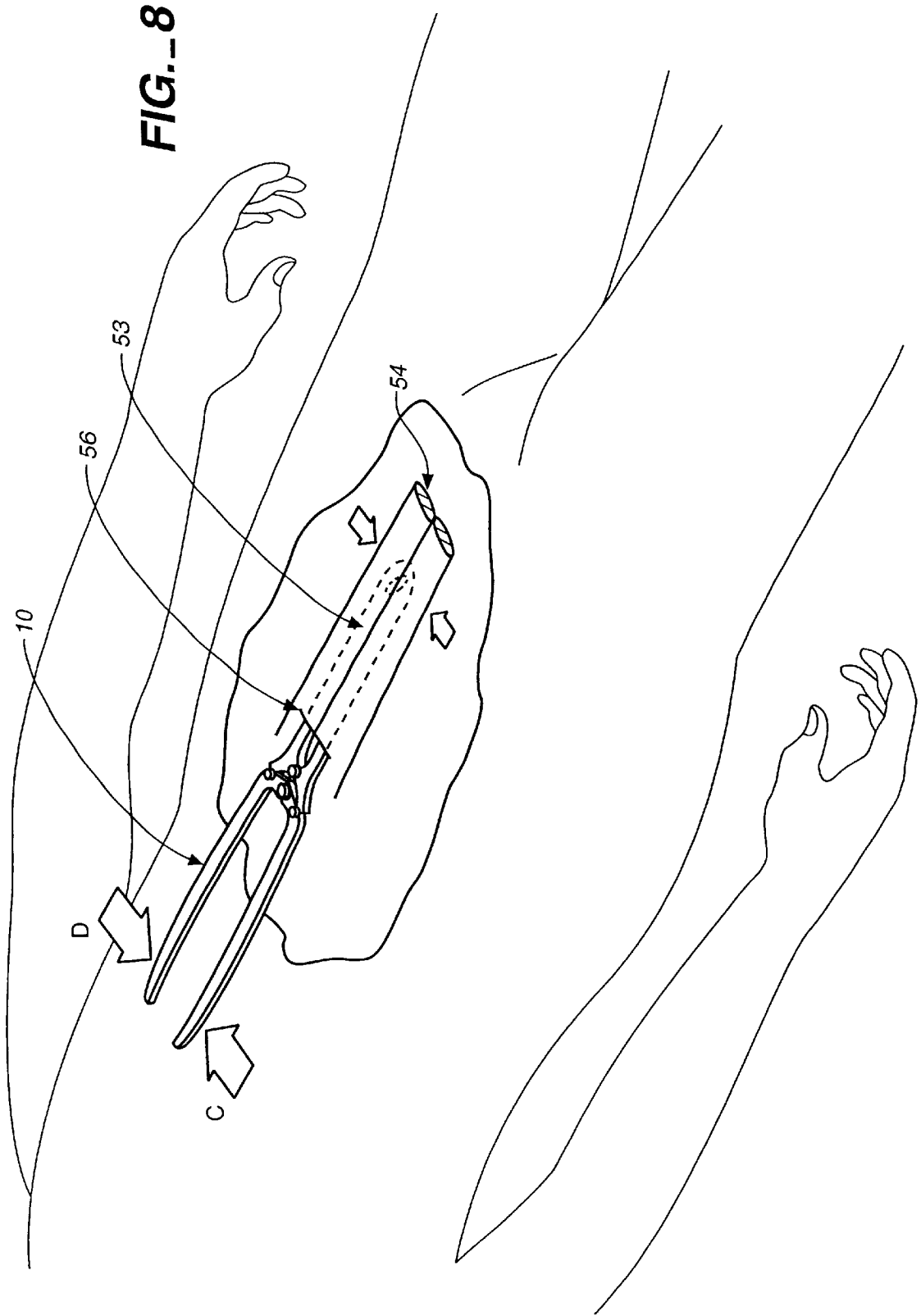
FIG._8

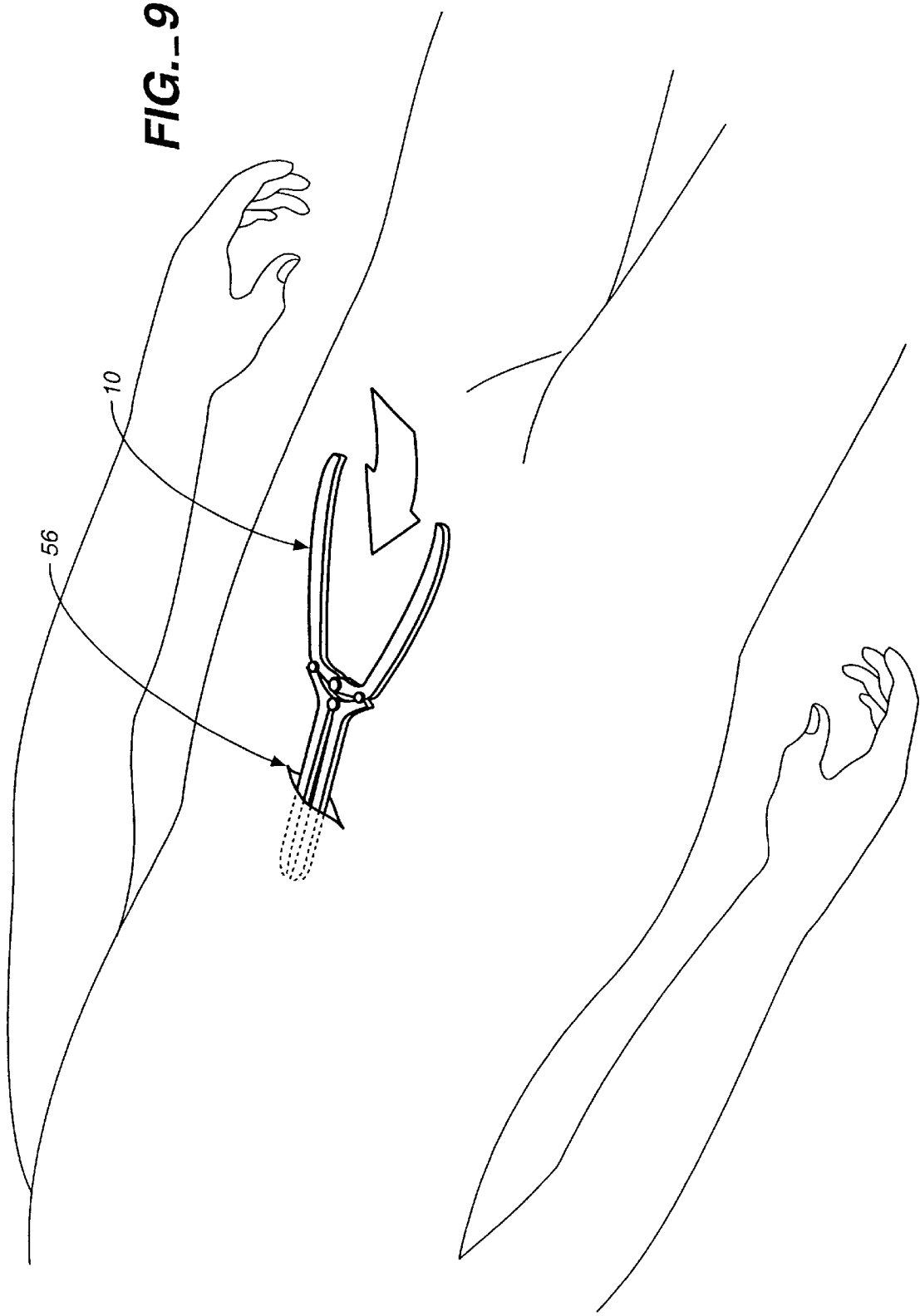

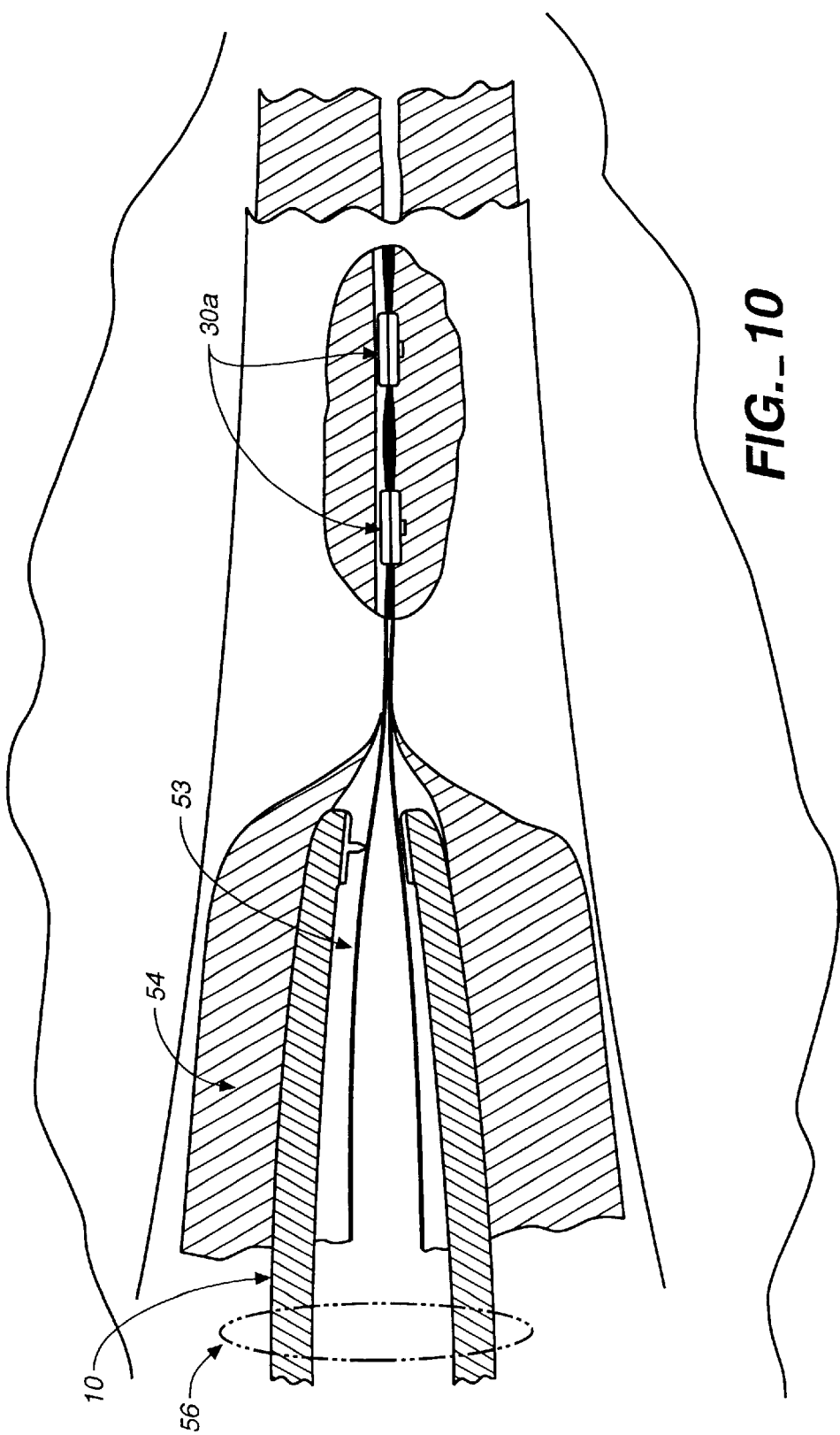
FIG._10

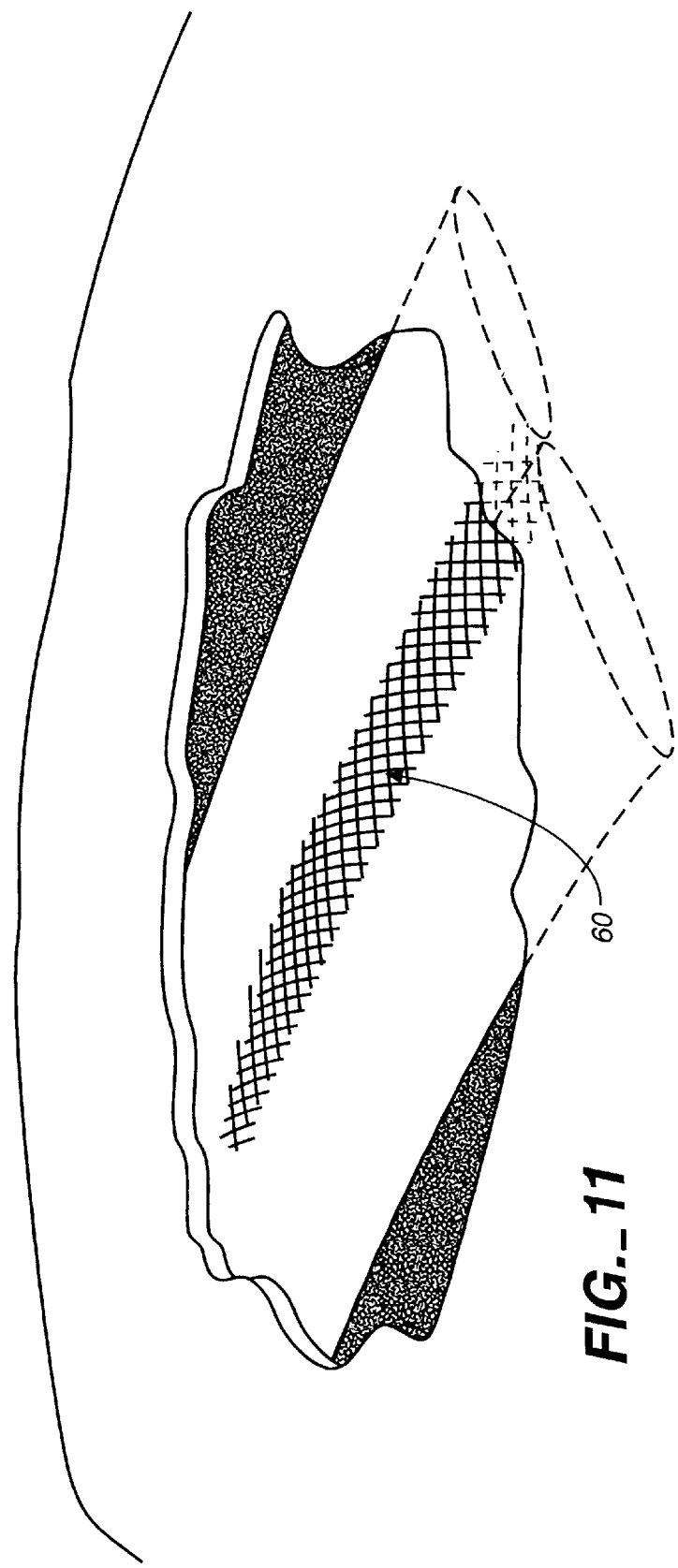
FIG._11

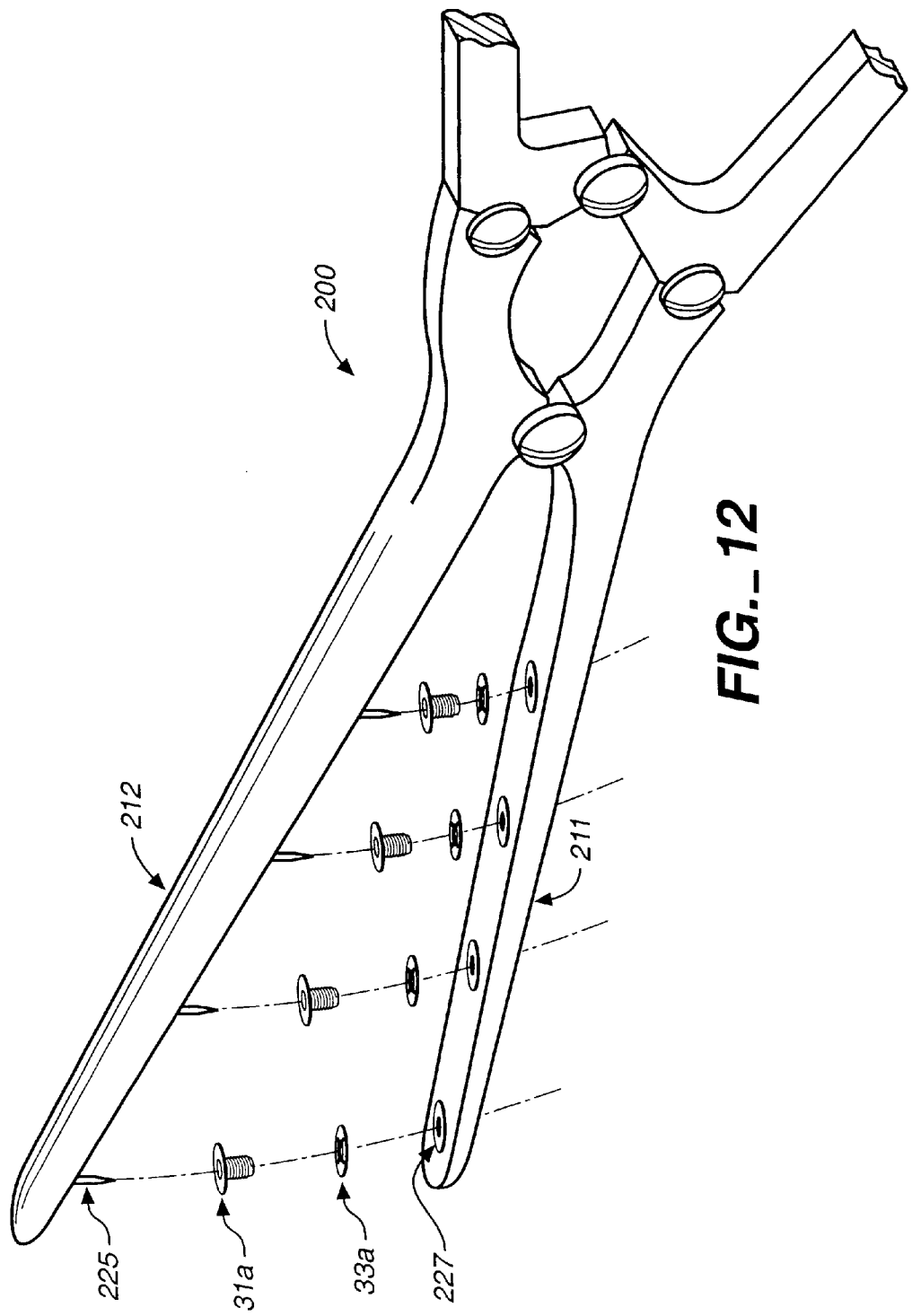
FIG._12

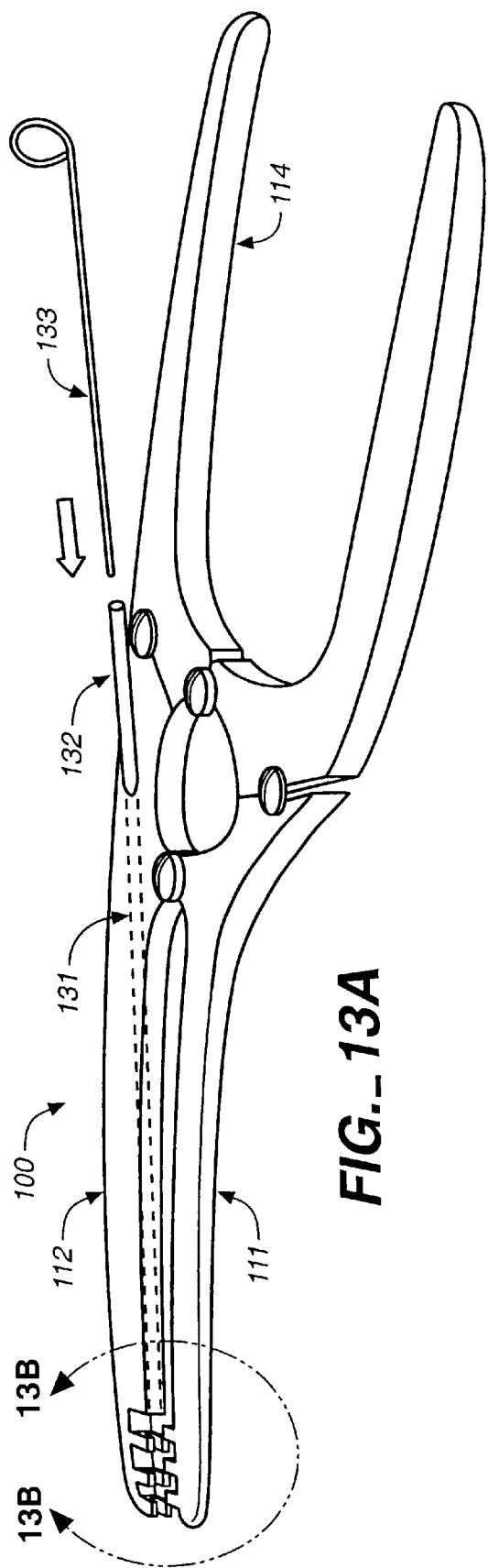
FIG._13A
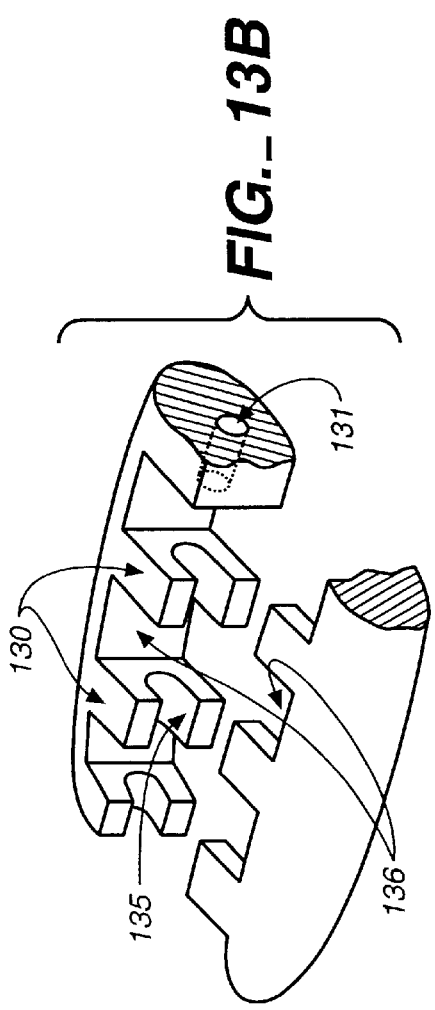
FIG._13B

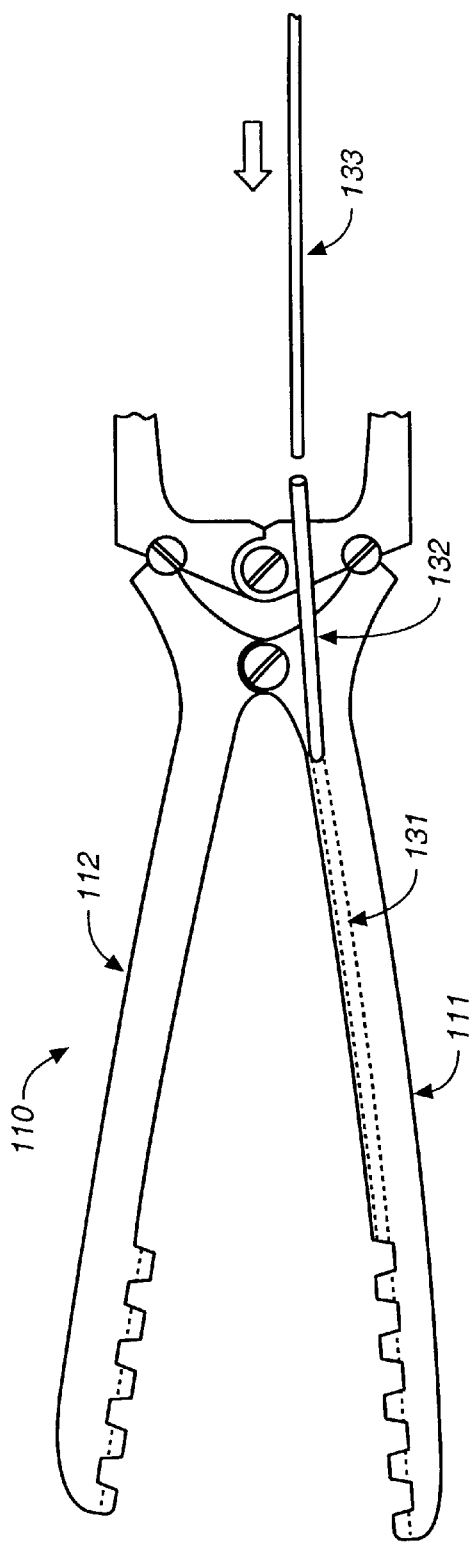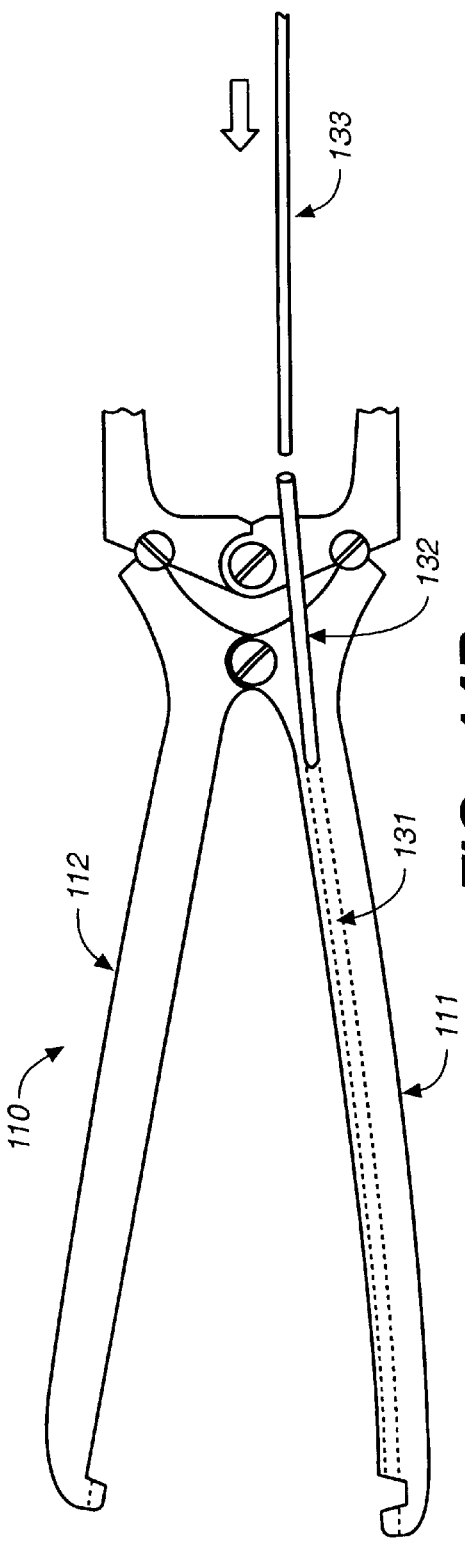

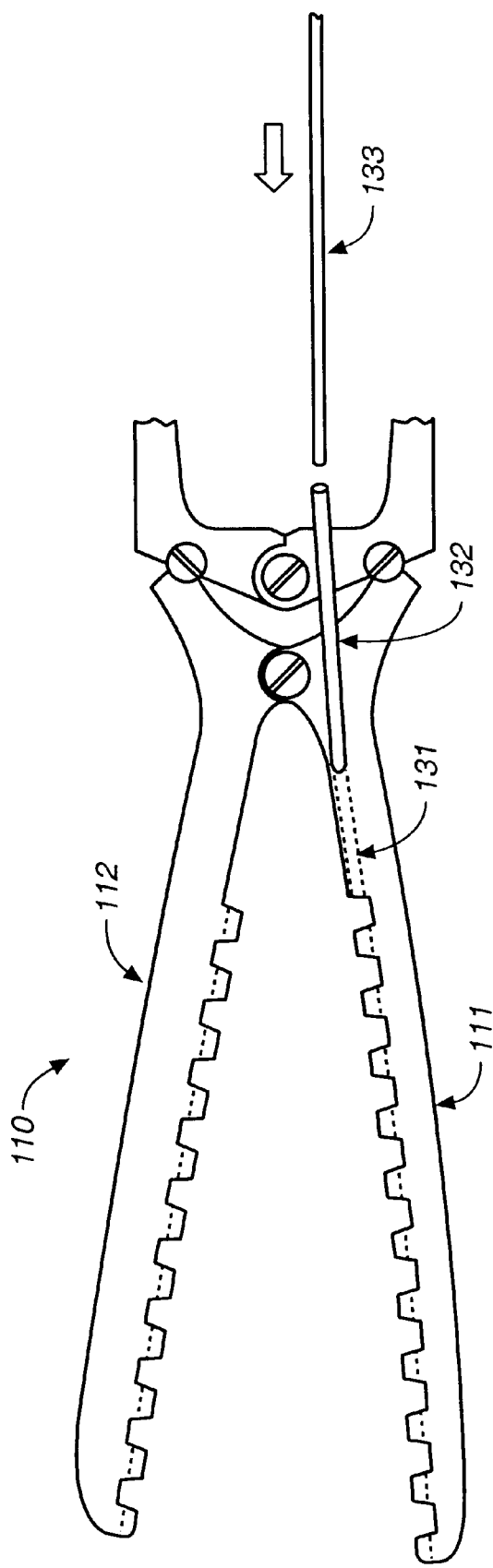
FIG._14C

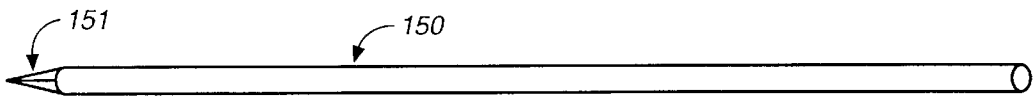
FIG._15A
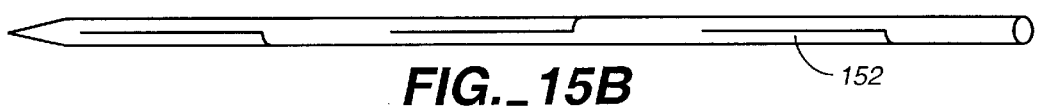
FIG._15B
FIG._15C
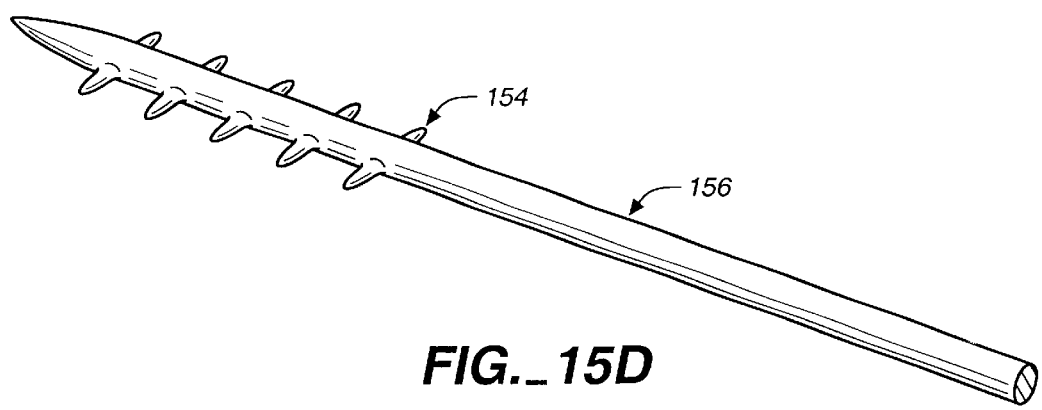
FIG._15D

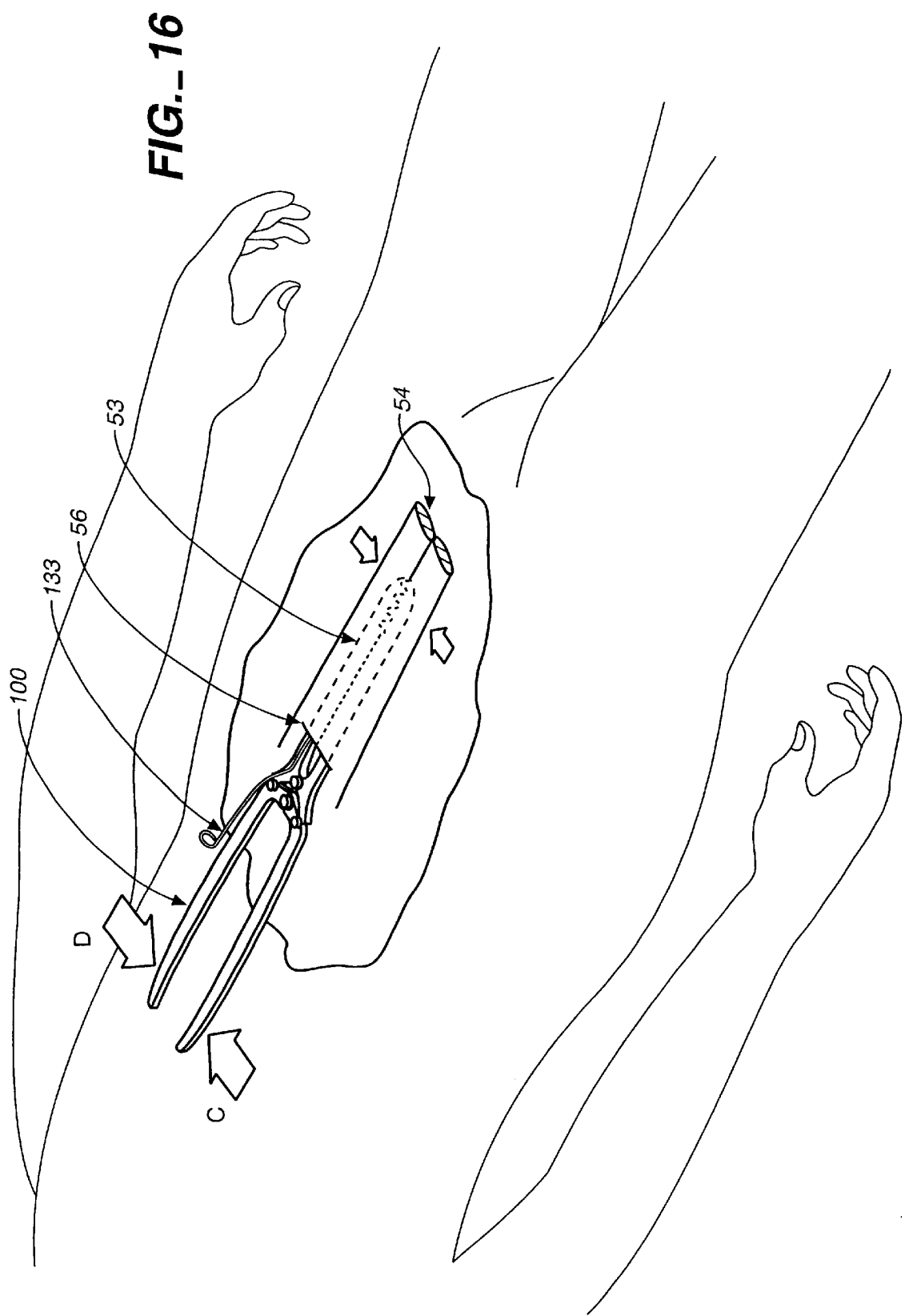
FIG._16

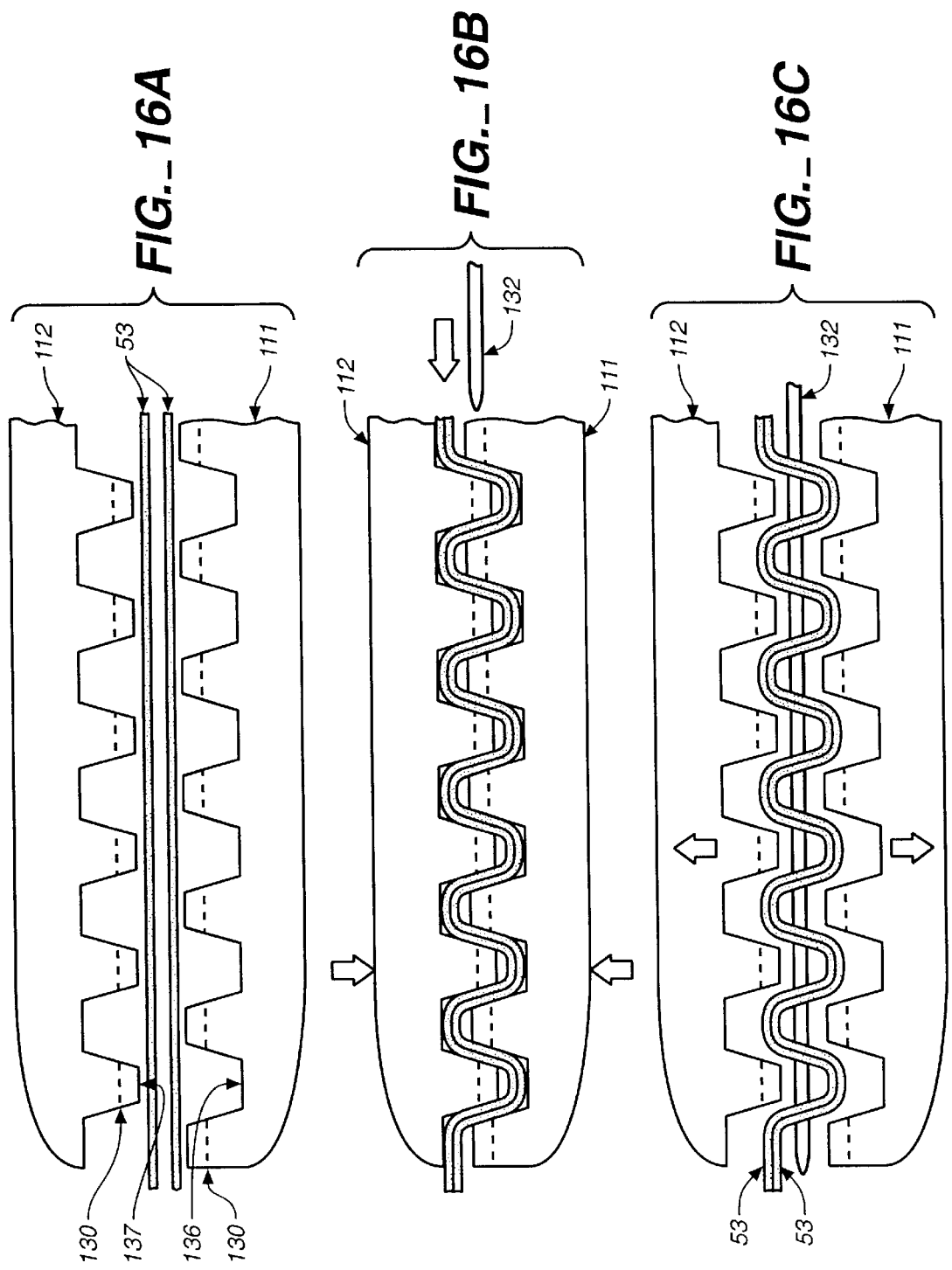

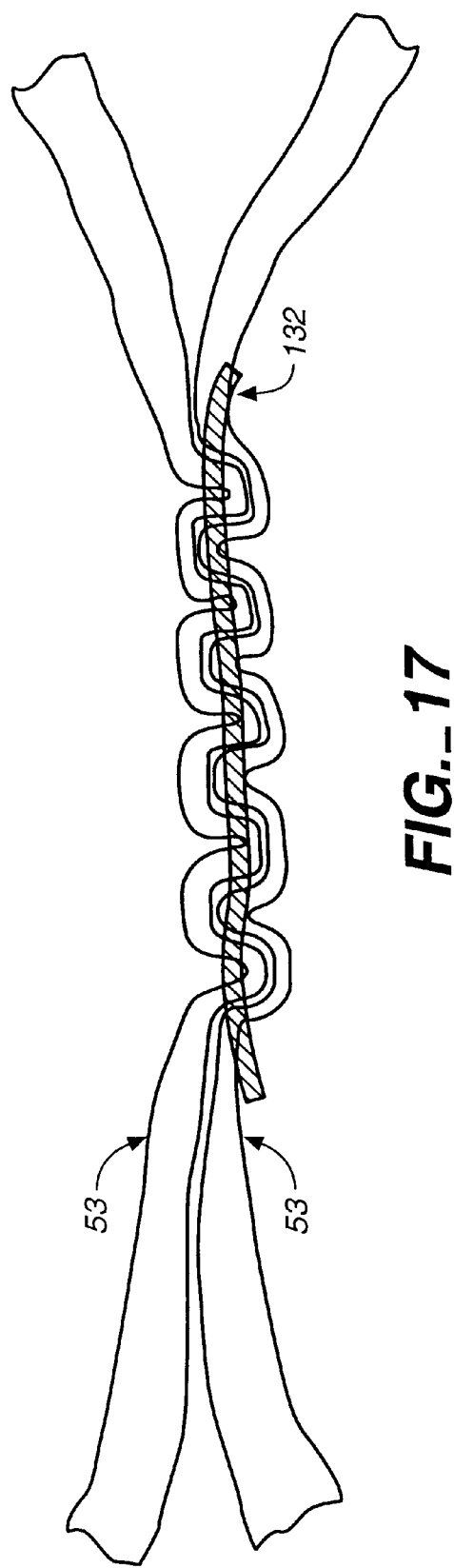

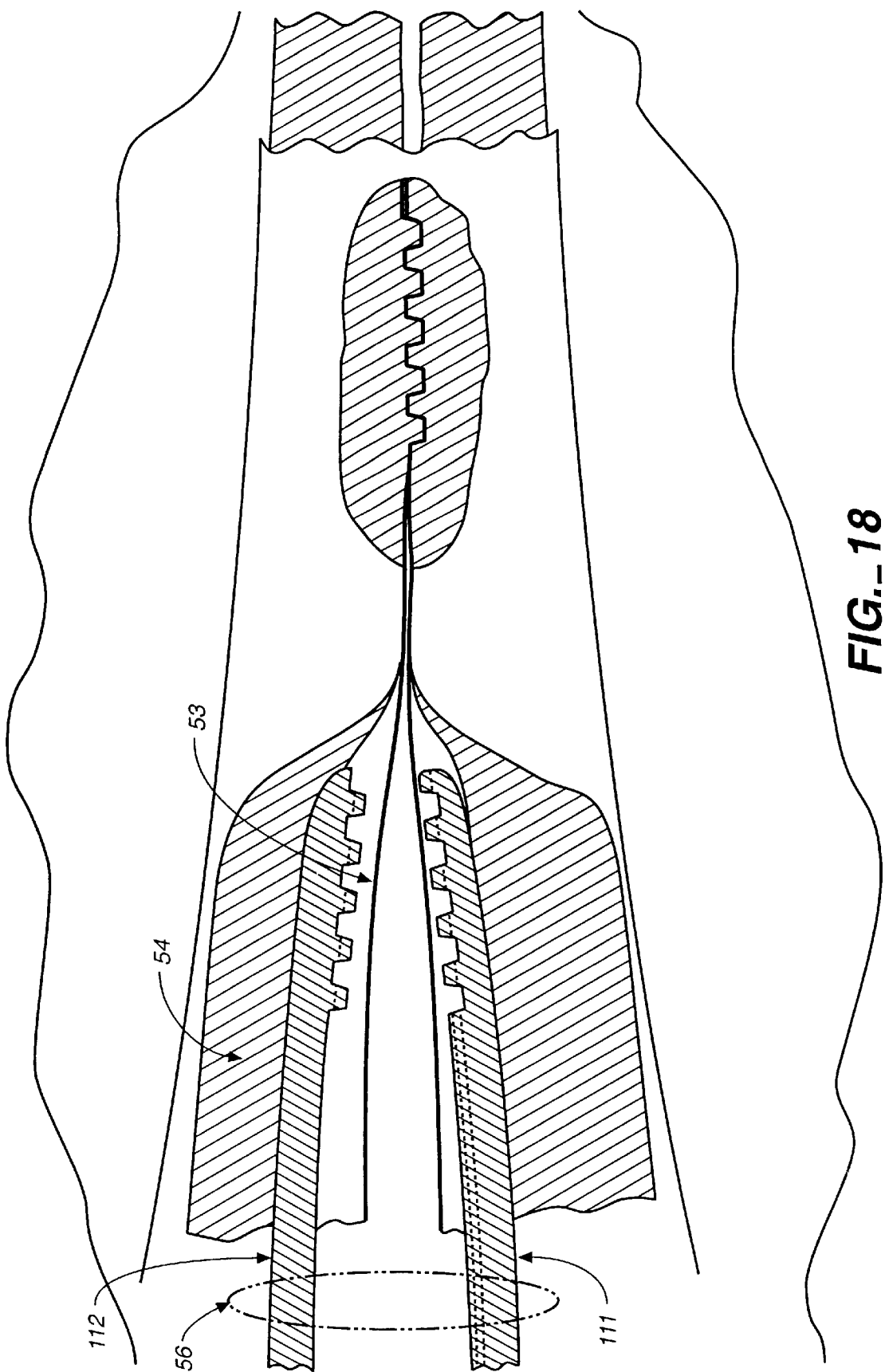
FIG._18

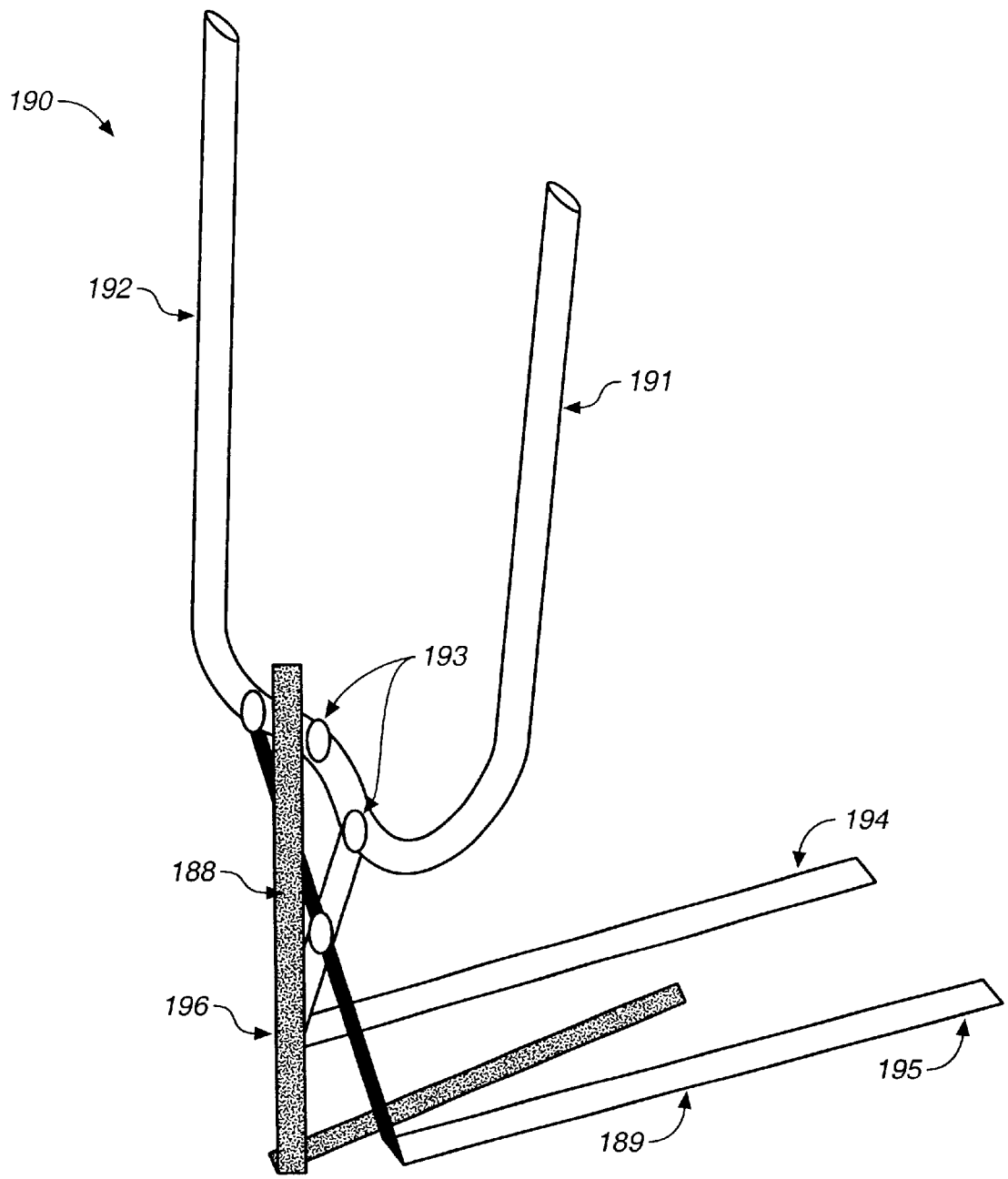
FIG._19

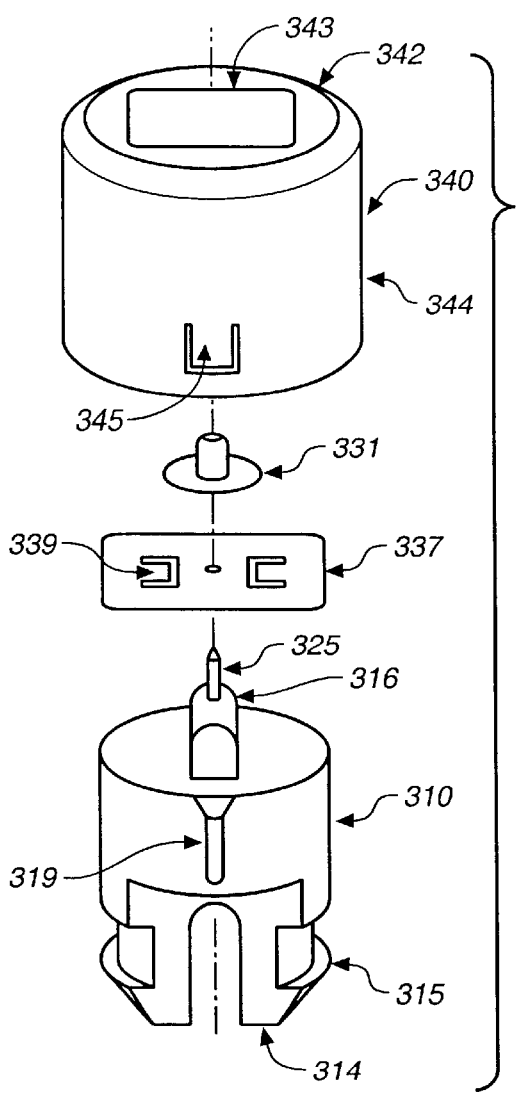
FIG._20
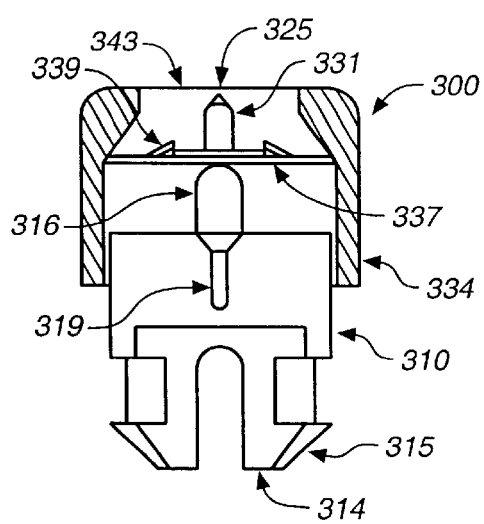
FIG._21
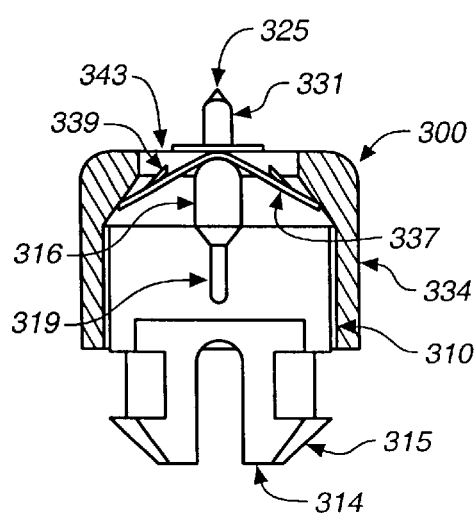
FIG._22

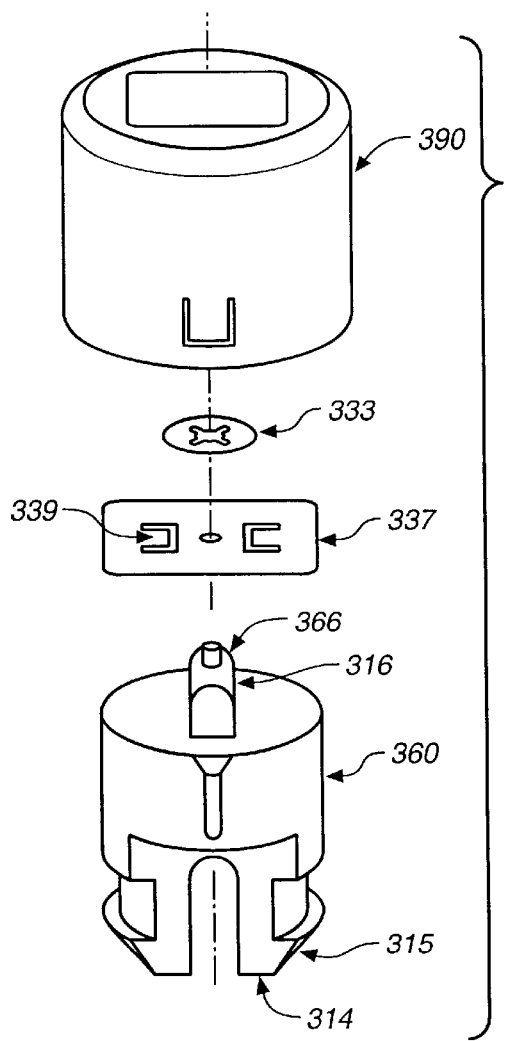
FIG._23
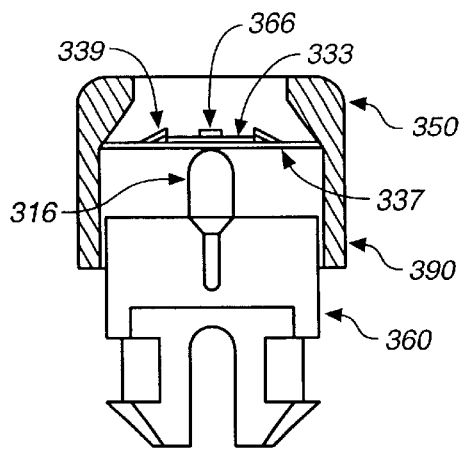
FIG._24
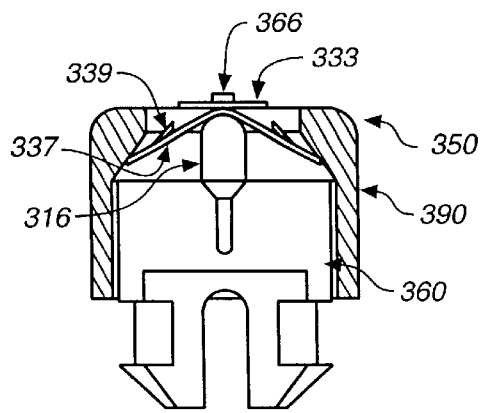
FIG._25

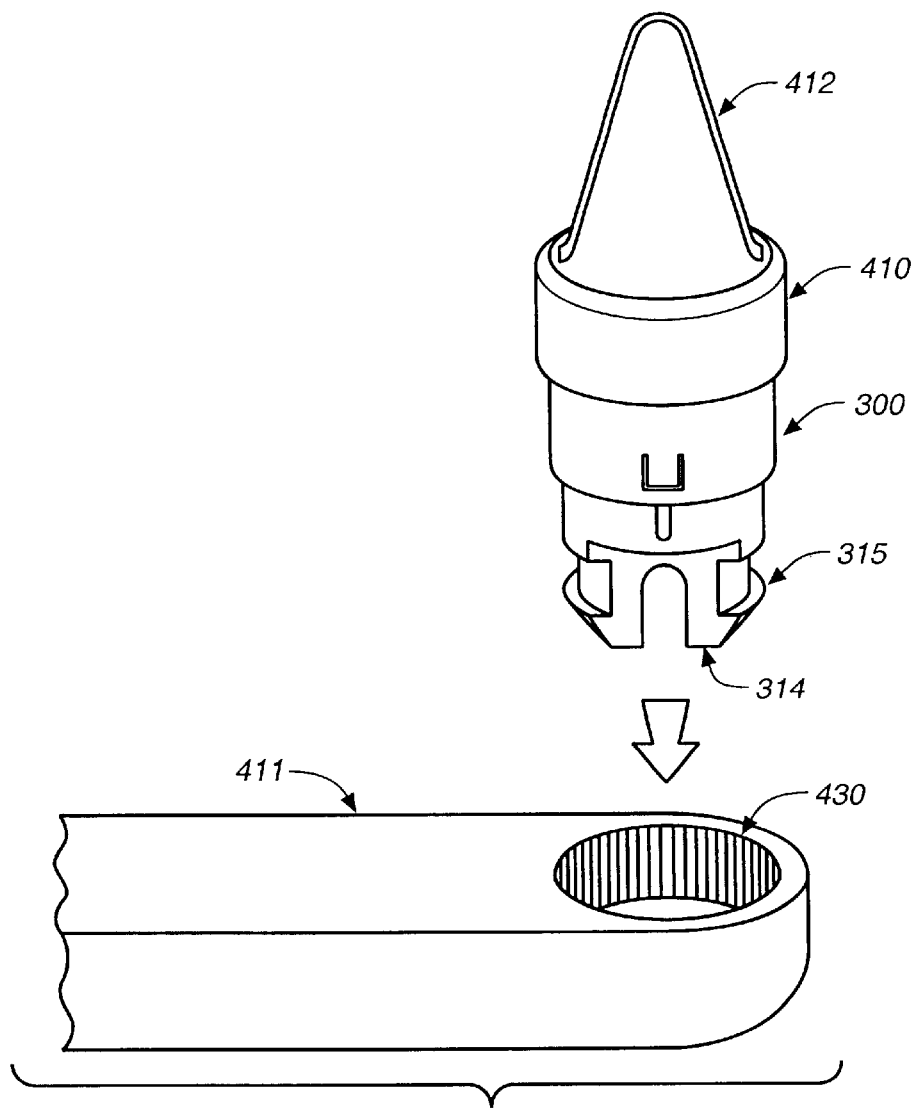
FIG._26
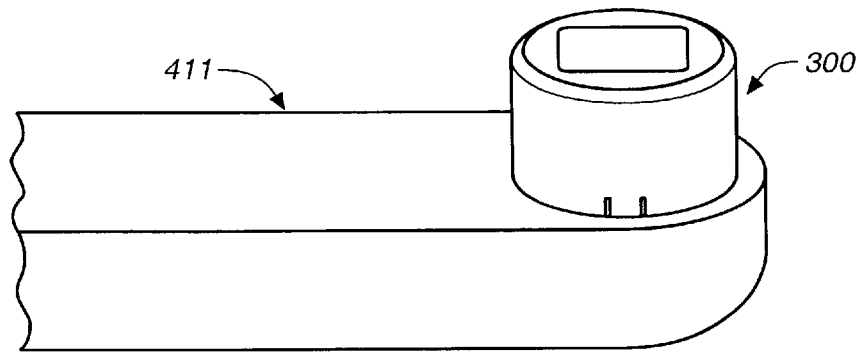
FIG._27

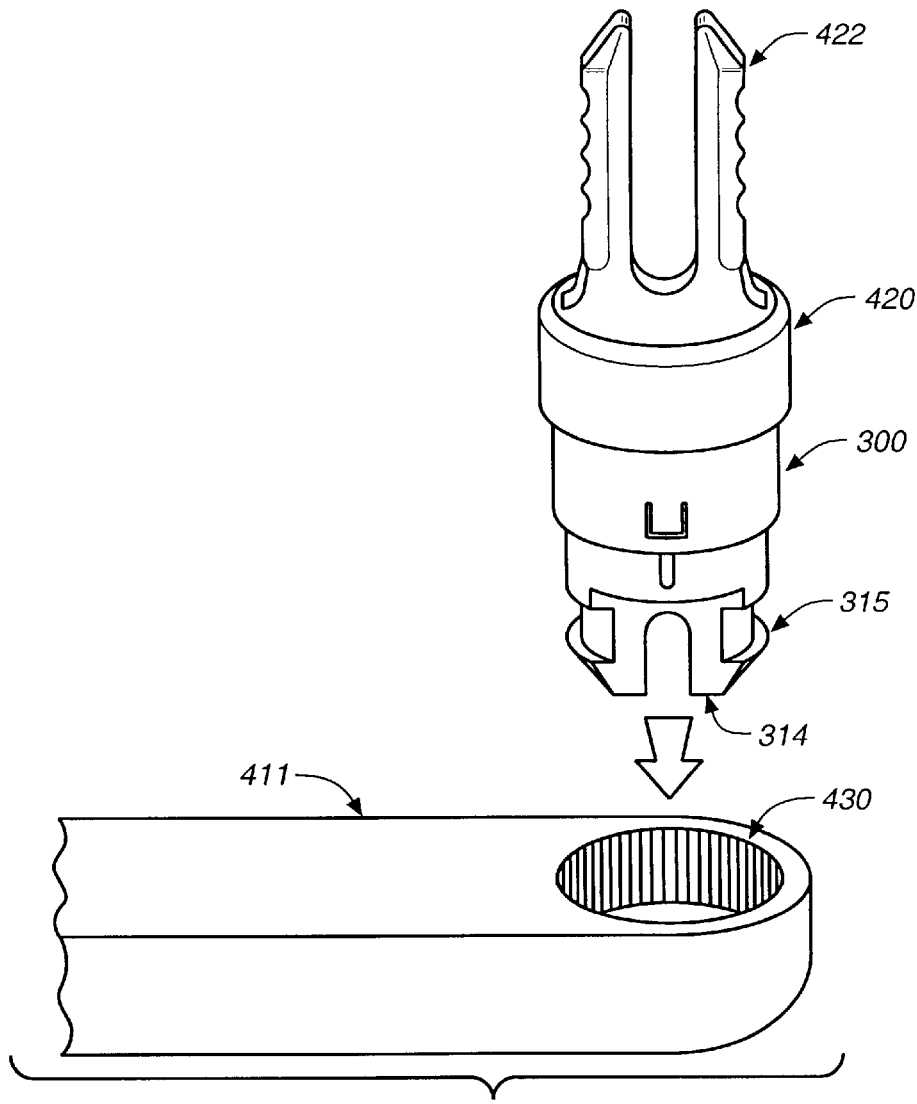
FIG._28
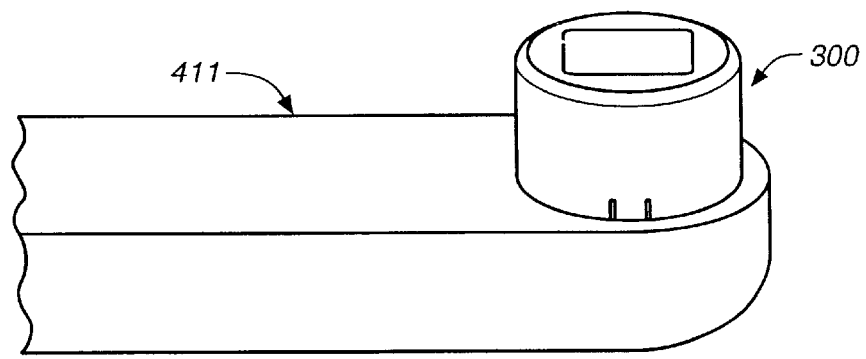
FIG._29

METHOD AND DEVICE FOR USE IN MINIMALLY INVASIVE APPROXIMATION OF MUSCLE AND OTHER TISSUE

The present application is a continuation of U.S. Application Ser. No. 09/738,818, filed on Dec. 15, 2000, now abandoned, which is a non-provisional and claims the benefit of priority under 35 U.S.C. §119(e) of U.S. Provisional Application No. 60/172,426, filed Dec. 17, 1999, each of which is incorporated herein in its entirety.

BACKGROUND OF THE INVENTION

The present invention relates generally to medical apparatus and methods and more particularly to devices and methods for the minimally invasive approximation of muscle, fascia or other tissue such as approximation of the rectus muscles in the abdomen (abdominoplasty), hernia repair, closing fascial defects and other such applications where fascia or other tissue structures need approximating, that provide patient benefit using minimally invasive techniques that, among other benefits, reduce or eliminate visible scars.

In the case of diastasis of the rectus muscle and ventral hernias, separation of muscles and fascia from each other can occur over time due to stretching or weakening of tissue, resulting in protrusion at the region of separation of otherwise contained material, e.g. fat, tissue, or intestine. For example, during pregnancy or over time with weight gain, the rectus abdominals muscles, (the large muscles that run longitudinally along the abdomen from the torso to the groin of a human being), can diverge from each other, resulting in a flabby appearance or in some cases protrusion of accumulated fat or other structures through the separated region. Many people desire to undergo surgical repair of the separated muscles either to repair the herniation of material, or in less extreme cases, purely for cosmetic reasons, sometimes in conjunction with liposuction or removal of excess skin and fatty tissue.

Historically, procedures such as abdominoplasty have been performed through a large open surgical incision in the abdomen, through which surgical tools are introduced to dissect away the subcutaneous tissue and fat from the abdominal fascia, and then directly reapproximating the medial borders of the rectus sheath, usually using sutures. Other methods for approximating fascia or otherwise joining body tissue are also known. For example, U.S. Pat. No. 5,125,553 describes a surgical instrument for joining body tissue for stapling a hernial opening in internal tissues of a patient. U.S. Pat. No. 4,127,227 describes a staple cartridge for applying staples to a large amount of fascia in a patient.

More recently, surgeons have performed abdominoplasty endoscopically by gaining access through a patient's umbilicus with the aid of a retractor and endoscope, and by making a smaller incision in the "bikini line" area to allow access for various surgical tools to dissect the muscles from the rectus fascia, as well as stapling tools to plicate the rectus fascia or suture the muscles together. As an example, U.S. Pat. Nos. 5,329,943 and 5,655,544 describe an endoscopic procedure for performing an abdominoplasty through two small incisions at the umbilicus and the "bikini line" areas of the patient. Approximation of the muscle and tissue is achieved by the use of a tenaculum (curved tip, sharp hemostat) and sutures or a stapling gun.

The abdominoplasty procedure can also be performed in conjunction with other procedures, such as liposuction, hernia repair or other reconstructive surgery.

While these techniques have been successful, there is a need for improved devices and methods for more efficiently performing procedures such as abdominoplasty that further reduce post-procedure scarring and allow for more rapid and comfortable patient recovery. It would be desirable to have a system of devices that allowed a physician to directly access the treatment site without leaving any visible scarring. Furthermore, it would be desirable to have a system of devices and methods that allowed tissue approximation procedures to be performed without the necessity of dissecting the subcutaneous tissue from the rectus fascia, thereby reducing trauma to the patient and speeding recovery time.

Such improved tools could access through a smaller incision, preferably at the umbilicus, where no visible scarring would ensue, and without the necessity of a second incision for visualization tools or other device maneuvers. In addition, to speed recovery time it would be desirable to focus the penetration and pulling together of fascia, directly on the fascia sheaths with minimal disruption of the rectus muscles themselves. Furthermore, it would be desirable to have tools that allow approximation of fascia even in the absence of a continuous loop of fascia, or in the case where the posterior rectus sheath does not fully extend or is not continuous in the area to be treated. This can be the case in the suprapubic region (below the umbilicus) where only the anterior portion of the rectus sheath extends.

Although such tools would be useful to approximate the tissue so that traditional suturing methods could be employed, it would also be desirable to have a system that included an implantable fastening member releaseably secured to the end of the tool for placement once the desired location of approximation is attained. It would furthermore be desirable for such devices to generate sufficient force to bias the fascia together as well as to deploy the fastener device to secure the fascia in its new position. Additionally, improved methods would be desirable for accessing the points of approximation through the rectus sheath of the abdominal rectus muscle, from within the fascia, as opposed to dissecting the subcutaneous tissue from the fascia more invasively and placing the approximating fasteners externally.

These and other objectives are met by the design and use of the various embodiments of the present invention, as detailed herein.

SUMMARY OF THE INVENTION

According to the present invention, improved methods and apparatus are provided for approximating tissue, fascia, muscle and the like. A first embodiment of the present invention provides a tissue approximating device or applicator tool, for use as a stand-alone device or tool or as part of a kit, for performing a minimally invasive abdominoplasty or similar procedure. The kit includes fastener devices, such as rivets or grommets, that can be placed from either side of a tissue surface while at the same time minimizing necessary exposed tissue surface and incision length in the patient. The applicator tool has opposing surfaces or jaws that are mounted for movement toward and away from one another by actuation of a handle member.

In an exemplary use of the present invention, a surgeon makes an incision along the margins of the umbilicus and makes an incision into the medial border of the rectus fascia of a patient and locates each jaw of the applicator tool into the envelope formed by the rectus sheath that surrounds the abdominus rectus muscles. This sheath encapsulates each length of abdominal muscle allowing each of the jaws to follow along the path formed between the sheath and the muscle, thereby minimizing the need for direct visualization once the tool is placed. Once located in their respective sheaths, the jaws of the tool can be advanced to the location where the first fastener is to be placed. The device can also be palpated from the skin surface by the surgeon to determine the location of the distal end of the tool relative to the muscle separation which has been previously determined. After placement of the first fastener, the procedure is repeated until the separated length of the abdominus rectus muscle has been approximated.

The present invention also incorporates an automated feature for releasing the fastening devices. The fastening devices can be formed in a series, such as in a cartridge, for easy loading into the jaws of the application tool. Alternatively, multiple fasteners can be deployed simultaneously from multiple deployment sites along the jaw of the applicator tool. The fastening devices may be formed of various materials and construction, including varying sizes, shapes and compositions.

In a yet another embodiment, the applicator tool distal jaw section may be formed in a notched configuration having a reciprocal tooth and cavity arrangements such that when the jaws of the tool are brought together, the distal ends of each tip reciprocally engage the other at the opposing notched or toothed section. The teeth contain recessed passageways, also referred to herein as "recesses" that allow the placement of a single fastening device in the longitudinal direction through tissue, as opposed to several fasteners deployed axially.

In a further embodiment, the applicator tool may be used simply to approximate the tissue or fascia without the secondary function of deploying a staple or other fastening device. In this embodiment, once the tissue is approximated using the biasing tool of the present invention, standard, suturing techniques may be employed to secure the tissue.

BRIEF DESCRIPTION OF THE DRAWINGS

FIG. 1 illustrates an applicator tool according to the present invention having a handle end and a working end, and a hinged section therebetween;

FIG. 1A is an expanded view of the distal end of the applicator tool of FIG. 1 showing retaining elements on each jaw tip for retaining tissue fastening members and a tissue guard feature;

FIG. 1B shows an alternative embodiment of the applicator tool of FIG. 1 having a tissue engaging rod for engaging and manipulating fascia;

FIG. 2 illustrates the distal portion of the applicator tool of FIG. 1 where the components of a tissue fastening member are releaseably attached to the retaining elements;

FIGS. 3A–3B illustrate different embodiments of a fastening member according to the present invention;

FIG. 4 illustrates a deployed tissue fastening member securing two approximated tissue layers together according to the teachings of the present invention;

FIG. 5A illustrates the anatomy of the normal relationship of rectus muscles within the rectus sheath;

FIG. 5B illustrates the anatomy of diastasis where the rectus muscles are separated;

FIG. 5C illustrates the anatomy of rectus muscles that have been reapproximated according to the present invention;

FIGS. 6–9 depict procedural steps of performing an abdominoplasty procedure according to the present invention using the applicator tool of FIG. 1;

FIG. 10 further illustrates an abdominoplaty procedure according to the present invention, including placement of the applicator tool jaws of FIG. 1 within the envelope of the rectus sheath and the abdominal rectus muscle, and the placement of several fastening members to approximate the muscles;

FIG. 11 illustrates the placement of a surgical mesh reinforcing member over the site of repair and implanted fasteners;

FIG. 12 illustrates an alternative embodiment of the applicator tool of FIG. 1 having multiple retaining elements such that multiple fasteners can be delivered simultaneously by a single actuation of the tool;

FIGS. 13A–13B illustrate an applicator tool according to a second embodiment of the invention having reciprocal teeth and cavities at the distal end of the tool that matingly engage and enable a fastening member to be threaded through said teeth to longitudinally fasten together tissue clamped therebetween;

FIGS. 14A–14C illustrate various alternative embodiments of the distal end of the applicator tool of FIG. 13, including embodiments having single and multiple teeth;

FIGS. 15A–15D illustrate alternative embodiments of a fastening member to be used in conjunction with the applicator tool of FIG. 13;

FIGS. 16 and 16A–16C illustrate a method of operating the applicator tool of FIG. 13 to approximate attenuated tissue surfaces;

FIG. 17 illustrates an embodiment of a fastening member according to the invention that that has been deployed to secure two approximated tissue layers;

FIG. 18 further illustrates the procedure of using the applicator tool of FIG. 13 to perform an abdominoplasty procedure including placement of the applicator tool jaws within the envelope of the rectus sheath and the abdominal rectus muscle, and placement of a longitudinal fastening member to secure the approximated muscles;

FIG. 19 illustrates a third embodiment of the present invention having a lever arm for engagement with fascia to facilitate approximation;

FIGS. 20–25 show embodiments of cartridge assemblies according to the present invention, where the assemblies house tissue fasteners; and FIGS. 26–29 show a cartridge assembly of FIG. 20 being inserted onto a jaw of an applicator tool of the invention using alternative embodiments of an insertion tool according to the invention.

DETAILED DESCRIPTION OF THE PREFERRED EMBODIMENTS

An exemplary applicator tool constructed in accordance with a first embodiment of the present invention is illustrated in FIG. 1. The applicator device 10 comprises a first handle portion and a first jaw member 12, operatively connected to a second handle portion 13 and second jaw member 11 by hinging means 16. Hinging means 16 may be a fixed hinge, or in some cases a releasable hinge mechanism, such as a removable pin, to allow the jaw members of the applicator tool to be placed separately within the rectus sheaths, and then linked together once they are placed at the point of the re-attachable hinge. The jaw members are likewise pivotally connected to their respective handle portions by hinging means 17.

In operation, the movement of the handle portions 13,14 toward one another causes force to be transmitted to the distal end of the jaw portions 11, 12 such that said jaw members move into contact with each other at their distal ends and/or continuing along the length of the jaw members depending on the jaw configuration and the number of fasteners to be deployed by a given actuation. Depending on the amount of tissue to be affected, the force needed can vary. Specifically in the case of abdominoplasty, the force generated at the distal end of the applicator tool is estimated to be in the range of between 10 to 80 pounds preferably in the range of 20–40 pounds.

As seen in FIG. 2, jaw members 11 and 12 have distal ends 21 and 23 and proximal ends 22 and 24. As illustrated retaining pin 25 is formed at distal end 21, for releasably securing a first fastening member 31 thereon. As depicted in FIG. 1A, a tissue guard 15 is positioned on and extends distal end 21 to shield the tissue from any trauma from the retaining pin and rivet as the device is passed into the tissue. Corresponding thereto and further shown in FIG. 2, a gripping surface 27 is formed on distal end 23 for releasably securing a second fastening member 33 thereon. Gripping surface 27 may be made of stainless steel or of a flexible material such as silicone, rubber or a thermoplastic elastomer. Alternatively, said gripping surface may be formed as a slot within the face of distal end 23, whereby said second fastening member is releasably retained thereon. Furthermore, distal end 23 may be provided with a through hole 29 adapted for receipt of retaining pin 25 when jaws are in a closed position.

In a preferred embodiment, the first fastening member is a hollow rivet and the second fastening member is a washer with a hollow center configured to matingly engage with the rivet (as more fully depicted in FIG. 3) when distal ends 21 and 23 are brought together. Other types of fastening members will be readily apparent to one skilled in the art. It is noted that depending on the desired configuration, the retaining member and gripping surface described above, can be mounted on either jaw of the application device.

An alternative embodiment of an application tool according to the present invention is shown in FIG. 1B. This tool is similar to that of FIG. 1A but further includes tissue engaging rod 8. Tissue engaging rod 8 includes handle 6 at the proximal end and tissue engaging portion 4 at the distal end. The rod is threaded through eyelet 2. The eyelet diameter is larger than the diameter of the rod itself allowing for a wide range of motion of the rod, including motion between the jaw members and above or below the plane created by the jaw members. The invention also contemplates other known means of attaching the rod to the tool to provide for a similar range of motion, such as pivotally mounting the rod to the tool. In operation, as more fully described herein, the eyelet can act as a fulcrum point about which the rod can be moved to force tissue downward (or upward) out of the way of the jaw members in order to facilitate accuation of the tool.

FIG. 3A depicts the preferred embodiment of fastener 30*a*. In this embodiment, fastener 30*a* comprises a first fastening member 31*a* and a second fastening member 33*a*. As depicted herein, the first fastening member 3*a* is a rivet, having a disk portion 35*a* connected to a stem portion 34*a* and a hollow lumen therethrough.

The preferred dimensions of first fastening member 31*a* are 0.125" to 0.3121, and 0.032 to 0.093 for the stem. In the preferred embodiment, said stem member may be threaded, or otherwise fitted with an irregular surface.

The second fastening member 33*a* comprises a flat disc washer having a hollow center 36*a* and open slots 38*a* extending from said hollow center such that the circumference of the hollow center forms an irregular border.

The preferred diameter of second fastening 33*a* member is 0.125" to 0.312" (disc), 0.032 to 0.093 (hollow center), with slots 38*a* extending 0.010" to 0.050" from the center of disc 36. In operation, slots 38*a* facilitate the mating engagement of first and second fastening members by frictionally engaging with the surface of stem 34*a* to form a permanent attachment to one another.

It should be noted that the fastener member can have several configurations depending on the application, for example discs 35 and 33 may be formed in an oblong, triangular or other shape to facilitate maximal interference with the target tissue once placed, as seen, for example, with fastener 306 shown in FIG. 3B. Furthermore, the fastener may be formed of stainless steel, Elgiloy, titanium or resorbable, implantable polymers. In an alternative embodiment as depicted in FIG. 12, multiple fastening members maybe disposed along jaws 111, 112 of applicator tool 100 to allow simultaneous deployment of the fasteners through tissue following a single actuation of the applicator handle.

It is desirable that the fastening members be sheathed or protected during positioning of the fastening members prior to deployment. Among other reasons, such sheathing aids in ensuring that the fastening members are not dislodged from the applicator tool before reaching the desired deployment site. Such sheathing also protects tissue from unnecessary trauma, for example, due to contact with a retaining pin, prior to the jaw members reaching the desired site for deployment of the fastening members.

One such sheathing assembly is depicted in FIGS. 20–28. As depicted, fastener cartridge assembly 300 of FIG. 20 includes cartridge body 310 and cartridge hood 340. Body 310 and hood 340 are typically formed of a durable plastic, such as a polycarbonate, that can be sterilized by autoclaving. Body 310 includes a base 312 having locking tabs 314 extending from the body. Driver body 316 extends away from the body in a direction generally opposite of the locking tabs. Retaining pin 325 extends from driver body 316 and receives spring clip 337 and rivet 331. Spring clip 337 can be made of, e.g., stainless steel or plastic that can be deflected under load but that will return to its original shape once the load is released. Rivet 331 snaps into tab slots 339 of clip 337 and the rivet/clip assembly is then mounted onto retaining pin 325 which extends through the center bore of the rivet and corresponding hole of the clip.

Cartridge hood 340 is configured to extend at least partially over cartridge body 310 and includes a top portion 342 having opening 343 and sidewalls 344 that extend over at least a portion of the main body of cartridge body 310. Tab 345 is cut into sidewall 344 and includes a detent (not shown), which engages slot 319 of body 310. FIG. 21 shows cartridge 300 in a non-deployed condition, with the clip and rivet fastener assembly nested inside cartridge hood 340 and the outer clip edges constrained by the interior shoulder of cartridge hood 340.

When sufficient force is exerted onto cartridge hood 340 against cartridge body 310, the detent of tab 345 releases from slot 319 and the cartridge hood moves toward cartridge body 310. As the driver body remains stationary, this movement of the cartridge hood results in driver body 316 pushing rivet out of opening 343, as depicted in FIG. 22. When the force is released, the tension in spring clip operates to return the cartridge hood 340 to its original position, shown in FIG. 21.

FIGS. 23–25 depict cartridge 350 having a similar assembly of cartridge hood and cartridge body. Cartridge 350 includes cartridge hood 390 and cartridge body 360, and a spring clip and fastening member assembly mounted on the body and nested within the hood 390. The difference in cartridge 350 is that clip 337 retains female washer 333 that fixedly mates with the stem of rivet fastener 331. Also, retaining pin 366 is deflectable, for example, it can be spring loaded or made of a deformable elastic material. When cartridge 300 and 350 are thus aligned opposite one another and are brought into contact, as happens when the cartridges are loaded onto the jaws of an actuator tool of the invention and the tool is actuated, the force exerted on the respective cartridge hoods moves the hoods relative to the cartridge bodies and rivet 331 and washer 333 are brought into contact and fixedly mated, thereby securing any tissue located between the two cartridges. In this process, deflectable retaining pin 366 is deflected out of the way by retaining pin 325, thereby releasing the washer. When the actuating force is mated released, the fastener is deployed and the retainer springs operate to return the cartridge hoods to their original positions.

As shown in FIGS. 26–29, insertion tools 410 or 420 can be used to insert a cartridge into a recession 430 located on jaw 41 of an applicator tool. The insertion tools are configured to correspond to and releasably retain the cartridge hood. Under force, lock tabs 314 snap into place on the jaw, with flanges 315 corresponding to an undercut portion (not shown) of recess 430 located at the distal end of jaw 411. Insertion tool 420 of FIG. 29 includes pincer arms 422 that can be manually manipulated to move toward one another. These arms can correspond to notches (not shown) on lock tabs 314 of the cartridge. By engaging the notches with the pincer arms of the insertion tool and bringing the arms together, the lock tab arms can be moved toward one another to "pop" the cartridge out of the jaw after use.

Once implanted, as depicted in FIG. 4, deployed fastener 30a brings together the fascia and any other tissue that is placed between the first and second engaging members. As currently depicted, tissue layer A and tissue layer B are brought into approximation by fastener 30a.

FIGS. 5A–5C illustrate the various anatomical locations depending on the status of approximation in each. FIG. 5A depicts a normal rectus abdominus section. FIG. 5B depicts a diastasis of the abdominal rectus muscles, leaving an area of weakness (W) therebetween. FIG. 5C depicts the anatomical location of the rectus abdominus related to the placement of the fastening devices of the present invention.

The method of use of the preferred embodiment of the present invention is illustrated in FIGS. 6–9. In FIG. 6, it should be noted that area (A) is drawn to have a transparent appearance to show the anatomical structures underneath comprising, rectus sheath 53 surrounding the rectus abdominus muscles 54. In practice of the invention, the only exposed incision location is at or near the patient's umbilicus or "belly button" in region 51. An umbilical incision 56 is made in the length of approximately 1 to 3 centimeters, such that once healed, the belly button will hide any scar that would be otherwise visible on the patient's abdomen. A larger incision may be made if additional tissue or fat removal is planned. Applicator tool 10 is placed into the incision as depicted in FIG. 7 and the jaw members are advanced between the rectus sheath and the abdominal rectus muscles to a point remote from the incision where the separated area to be treated is located.

As shown in FIG. 8, the applicator tool is then actuated as indicated by arrows C and D, bringing the rectus sheath together resulting in approximation of the abdominal rectus muscles.

FIG. 9 depicts insertion of the applicator tool in the opposite direction through the existing umbilical incision to approximate fascia in the upper abdomen.

FIG. 10 depicts a detailed view of the use of the application tool present invention. Application tool 10 is inserted through the umbilical incision 56 and is advanced in the annular space created by the device 10 between the abdominal rectus muscle 54 and the rectus sheath 53. Fastening members are then installed by operation of the application tool along the length of the separation to be treated, approximately every 1 to 3 centimeters. As the application tool is actuated the fastening member draws the fascia and other tissue together and secures the rectus sheath together, thereby pulling the abdominal rectus muscles into approximation with each other retaining pin 25 pieces the fascia, allowing the reciprocal fastening members to engage and fixedly mate. Optionally, as depicted in FIG. 11, a prolene-type mesh member such as hernia mesh 60, can be placed across the approximated region to increase healing (scar tissue) at the fastener site, thereby relieving the stress on the fasteners and spreading it over the area of the mesh. The mesh can be either placed with fasteners or glued (not shown). The mesh can be placed over any number of fastening devices disclosed as part of the present invention.

As previously mentioned, application tool 100 of FIG. 1B can be used to facilate approximation where there may be more extensive amounts of fascia or other tissue separating the abdominal muscles. In such situations, tissue engaging rod 8 can be manipulated to engage and force the fascia downward below the plane of the jaw members and rectal muscles. This action both moves fascia out of the jaw path to facilitate acuation as well as create a pulling action transmitted by the fascia to the rectal sheaths that itself aids in bringing the rectal muscles into closer proximation.

A second embodiment of an applicator tool constructed in accordance with the present invention is illustrated in FIGS. 13A–13B. In this embodiment, applicator tool is provided with a distal tip having a reciprocating tooth/cavity configuration. The distal end of first jaw 112 and second jaw 111 are cut out in an alternating pattern to form teeth 130 and northes or cavities 136 that reciprocally engage one another when the jaws are brought together. As with the tool of FIG. 1A, the first and second jaws may be separately placed and then hooked together at the pivoting point. Between each tooth member 130, there is a cut away section forming a cavity 136 that is positioned relative to the tooth member of the opposing jaw to receive said opposing tooth member when the jaws of the applicator tool are in a closed position. At least one jaw of the applicator tool includes lumen 131 extending longitudinally along at least part of the length of the jaw length and terminating near the attachment point of handle member 14. A longitudinal fastener 132 can then be threaded through the lumen 131, using pusher member 133. As depicted in FIG. 13A, as lumen 131 extends up to the toothed section in the distal portion of the jaw, where it is axially aligned with passageway or recess 135 in teeth 130. In operation, this allows the fastener to remain in place following its longitudinal deployment through lumen 131 and recess 135 when the jaws are in a closed position. Each recess 135 opens toward the opposing jaw member which further allows the jaws to be reopened following longitudinal fastener deployment once the fastener 132 has been deployed through the toothed section of the jaw, just beyond the termination point lumen 131. Depending on the amount of tissue to be affected in one actuation of the applicator tool, the reciprocating tooth/cavity section length may vary, e.g., medium length (FIG. 14A), a single section (FIG. 14B) or maximal length (FIG. 14C).

FIGS. 15A–15D depict various embodiments of longitudinal fastener 132. FIG. 15A shows a single longitudinal fastener 150, having a sharp distal end 151 for piercing tissue as it is advanced through lumen 131 and into the tissue clamped in the recess 135 and the cavity 136 of the clamp jaw. It may be further advantageous to provide an anchoring means along the length of fastener 132 to ensure that the fastener remains localized in the tissue to be approximated once the fastener is deployed. Such anchoring structures 153 are depicted in FIGS. 15B (constrained position) and 15C (deployed condition) as longitudinal slits 152 along the length of the fastener that are formed to spring out away from the main body of the fastener once placed, In an alternative embodiment, the anchoring structures may be formed as protrusions 154 along the length of fastener 156 depicted in FIG. 15D. These protrusions may be flexible enough to deform upon deployment through the jaw through lumen, but resilient enough to expand and engage the tissue once fully deployed. The longitudinal fastening members may be formed of various materials, including spring steel, stainless steel, NiTi, Elgiloy or sufficiently rigid plastics or other implantable polymers.

Further, in yet an alternative embodiment, the longitudinal fastener may be formed of standard suture material. In this embodiment, the suture would be threaded through a needle member (not shown) and advanced along the jaw through lumen 131 and retracted once the suture was placed, leaving only the suture member in place at the end of the procedure.

In operation, and as shown in FIG. 16 applicator tool 100 is advanced through an umbilical incision and each jaw of the applicator tool is advanced within the annular space created by the tool between the abdominal rectus muscle and the rectus sheath as previously described in conjunction with FIGS. 6–9. FIG. 18 shows in more detail the operation of this method after insertion of tool into the rectus sheath and advancement to the point of the necessary reapproximation of tissue. In FIG. 16A the toothed sections 130 of the applicator tool jaws are aligned within rectus sheath 53 and actuated to move together, clamping the tissue of the rectus sheath 52 within cavities 136 of the toothed jaw, and the corresponding crowns of the teeth 130. FIG. 16B depicts the advancement of the longitudinal fastener 132 along lumen 131 of the jaw and through the recesses (not shown) and jaw cavities 136, engaging any tissue of the rectus sheath clamped therebetween. The jaws of the applicator tool are then released as illustrated in FIG. 16C, leaving the longitudinal fastener in place and approximating the rectus sheath. A cross section of the approximated tissue according to this secondary embodiment is shown in FIG. 17.

In some cases, it may be necessary to use a modified version of the applicator tool described herein as depicted in FIG. 19. In these cases the posterior rectus, sheath portion is not coextensive with the anterior rectus sheath in the area to be treated, typically in the suprapubic region of the abdomen. FIG. 19 depicts an applicator tool having a lever arm 196 attached to or used in conjunction with said applicator tool, to assist in the desired tissue approximation in the absence of a continuous rectus sheath to lever the tissue together as previously described. As shown in FIG. 19, applicator tool 190 has a first handle 191 and a second handle 192 connected by a hinged section 193 to a first jaw 194 and a second jaw 195. Jaws 194 and 195 may be formed with a perpendicular section 188 and a parallel section 189 to allow the user increased leverage over the tissue. In addition, either as a separate tool, or a part of the applicator tool (e.g. joined at the hinge section 193) lever arm 196 is provided to assist the procedure. In operation, lever arm 196 can be placed longitudinally with respect to the rectus muscles and actuated in an upward movement toward the anterior rectus sheath, creating an inverted IV, in the tissue and thereby tightening the fascia to form an edge over the anterior wall fascia and allowing the jaws to come together and secure the anterior fascial layer together.

Optionally in this configuration, the perpendicular portion of either the first jaw or the second jaw may be detachable to allow for the jaws to be placed separately and then connected and the hinged section 193, once each is placed at the desired treatment site. Such a device and method may also be used anywhere in the body where you want to approximate fascia where it is not continuous along the length of the site to be treated.

While the above is a complete description of the preferred embodiments of the invention, various alternatives, modifications, and equivalents may be used. Therefore, the above description should not be taken as limiting the scope of the present invention.

We claim:

1. A tissue approximating device comprising:

first and second jaw members, said first and second jaw members being moveable toward and away from one another;

a first and second retaining means, said first and second retaining means being located generally opposite one another on said first and second jaw members, respectively;

first and second fastening members releasably secured to said first and second retaining means, respectively, said engaging means being configured such that when said first jaw member is moved toward said second jaw member, said first fastening member fixedly mates with said second fastening member; and a tissue engaging rod having a tissue engaging portion that can extend generally parallel to said first and second jaw members and that is moveable from a first to second position.

2. The tissue approximating device of claim 1 wherein said tissue engaging rod is pivotally attached to said first and second jaw members.

3. A method of approximating the abdominal rectus muscles of a patient by adjoining the overlying tissue and rectus sheath surrounding said abdominal rectus muscles comprising:

forming an incision in the abdomen of a patient;

providing an applicator tool having first and second jaw members, said jaw members being moveable toward one another upon actuation of said applicator tool, and at least one pair of fastening members releasably attached to said first and second jaw members, respectively, said fastening members being configured to fixedly mate upon engagement with one another;

inserting said applicator tool into said incision;

advancing said jaw members along the length of the abdominal rectus muscles within the rectus sheath;

actuating the applicator tool such that upon actuation said first and second jaw members move toward one another and at least one of the fastening members pierces the wall of the rectus sheath and fixedly mates with the other fastening member thereby fastening said rectus sheath tissue therebetween; and removing said applicator tool from the incision.

4. A method of approximating tissue according to claim 3 wherein said step of providing an applicator tool further comprises providing an applicator tool further having a tissue engaging rod having a tissue engaging portion that can extend generally parallel to said first and second jaw members and that is moveable from a first to second position; and further comprising the step of, after advancing the jaw members along the abdominal rectus muscles within the rectus sheath but prior to actuating the applicator tool, moving the lever arm such that tissue between said jaw members is engaged by the tissue engaging portion of said tissue engaging rod and is pressed downward.

5. A tissue approximating device comprising:
first and second jaw members moveable toward one another, said first and second jaw members having inner surfaces facing toward one another other, said inner surfaces of said first and second jaw members having at least one tooth member and at least one reciprocal cavity member, respectively, such that when the inner surfaces of said first and second jaw surfaces are moved toward one another said at least one tooth member on said first jaw member is received at least partially within said at least one reciprocal cavity member of said second jaw member, and further wherein said first jaw member includes a lumen extending longitudinally through at least a portion of the first jaw member.

6. The tissue approximating device of claim 5 wherein said at least one tooth member of said first jaw member includes a recessed passageway extending longitudinally of the tooth member and opening toward both proximal and distal ends of said first jaw member, said passageway being axially aligned with said lumen.

7. A tissue approximating kit comprising:
a tissue approximating device having first and second jaw members moveable toward one another,
said first and second jaw members having inner surfaces facing toward one another other, said inner surfaces of said first and second jaw members having at least one tooth member and at least one reciprocal cavity member, respectively, such that when the inner surfaces of said first and second jaw surfaces are moved toward one another said at least one tooth member on said first jaw member is received at least partially within said at least one reciprocal cavity member of said second jaw member, and a lumen extending longitudinally through at least a portion of the first jaw member; and
an elongate fastening member adapted to be slidably received within the first jaw member lumen and the passageway of said tooth member.

8. The tissue approximating kit according to claim 7 wherein said fastening member further comprises an elongate body having restraining elements that extend from the body.

9. The tissue approximating kit according to claim 8 wherein said tissue approximating device further comprises a tissue engaging rod, said tissue engaging rod having a tissue engaging portion that can extend generally parallel to said first and second jaw members and that is moveable from a first to second position.

10. The tissue approximating kit of claim 9 wherein said tissue engaging rod is pivotally attached to said first and second jaw members of said tissue approximating device.

11. A method of approximating the abdominal rectus muscles of a patient by adjoining the overlying tissue and rectus sheath surrounding said abdominal rectus muscles comprising:
forming an incision in the abdomen of a patient;
providing an applicator tool having
first and second jaw members moveable toward one another, said first and second jaw members having inner surfaces facing toward one another other, said inner surfaces of said first and second jaw members having at least one tooth member and at least one reciprocal cavity member, respectively, said first jaw member further having a lumen extending longitudinally through at least a portion of said first jaw member, and said at least one tooth member further including a passageway extending longitudinally of the tooth member and opening toward both proximal and distal ends of said first jaw member, said recessed passageway being axially aligned with said lumen;
advancing said jaw members along the length of the abdominal rectus muscles within the rectus sheath;
actuating the applicator tool such that upon actuation, said first and second jaw members are moved toward each other, and at least one tooth member on said first jaw member is received at least partially within said at least one reciprocal cavity member of said second jaw member with a portion of said rectus sheath being located therebetween;
providing an elongate fastening member configured to be received through said first jaw member lumen;
advancing said fastening member through said first jaw member lumen and said tooth member passageway and through any tissue located therebetween.

12. A fastener cartridge for insertion onto a jaw member of a tissue approximation device, the fastener cartridge comprising:
a cartridge body, said cartridge body having a base configured for attachment to the jaw member and a driver member, said driver member having a fastener pin extending therefrom,
a retainer spring;
a fastner member releaseably secured to said retainer spring and to said fastner pin; and
a cartridge hood, said cartridge hood having a top surface with an opening and sidewalls extending at least partially over said cartridge body such that said retainer spring, fastner member and driver member are disposed within said cartridge hood.

13. The fastener cartridge of claim 12 further comprising means for maintaining said cartridge hood and said cartridge body in a fixed relationship to one another.

14. The fastener cartridge of claim 12 further comprising a lock tab on said cartridge and reciprocal recess on said cartridge body, said lock tab engaging said recess to maintain said cartridge hood and said cartridge body in a fixed relationship to one another.

15. A tissue approximation kit comprising:
at least two fastner cartridges according to claim 12; and
a tissue approximating device having first and second jaw members being moveable toward and away from one another and recesses at the distal ends of the jaw members configured to retain said fastener cartridges.

16. The tissue approximation kit of claim 15 wherein at least one fastner cartridge contains a first fastening member and at least a second fastener cartridge contains a second fastening member, said first and second fastening members configured to fixedly engage one another.

17. A tissue approximating device comprising:
first and second jaw members moveable toward one another, said first and second jaw members having inner surfaces facing toward one another other, said inner surfaces of said first and second jaw members having at least one tooth member and at least one reciprocal cavity member, respectively, such that when the inner surfaces of said first and second jaw surfaces are moved toward one another said at least one tooth member on said first jaw member is received at least partially within said at least one reciprocal cavity member of said second jaw member, and a tissue engaging rod, said tissue engaging rod having a tissue engaging portion that can extend generally parallel to said first and second jaw members and that is moveable from a first to second position.

18. The tissue approximating device of claim 17 wherein said tissue engaging rod is pivotally attached to said first and second jaw members.

* * * * *